United States Patent
Kim et al.

(10) Patent No.: US 11,071,754 B2
(45) Date of Patent: Jul. 27, 2021

(54) METHOD OF GENERATING TUMOR-SPECIFIC T CELLS

(71) Applicant: CASE WESTERN RESERVE UNIVERSITY, Cleveland, OH (US)

(72) Inventors: Julian Kim, Cleveland, OH (US); Kevin Choong, Cleveland, OH (US); Hallie Graor, Cleveland, OH (US); Mei Zhang, Cleveland, OH (US); John Ammori, Cleveland, OH (US); Anthony Visioni, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/954,274

(22) Filed: Apr. 16, 2018

(65) Prior Publication Data
US 2018/0228844 A1    Aug. 16, 2018

Related U.S. Application Data

(63) Continuation-in-part of application No. 14/205,069, filed on Mar. 11, 2014, now Pat. No. 9,944,898.

(60) Provisional application No. 61/776,352, filed on Mar. 11, 2013, provisional application No. 62/560,943, filed on Sep. 20, 2017.

(51) Int. Cl.
*A61K 35/17* (2015.01)
*C12N 5/0783* (2010.01)
*A61P 35/00* (2006.01)

(52) U.S. Cl.
CPC .............. *A61K 35/17* (2013.01); *A61P 35/00* (2018.01); *C12N 5/0636* (2013.01); *C12N 5/0638* (2013.01); *C12N 2501/165* (2013.01); *C12N 2501/2302* (2013.01); *C12N 2501/51* (2013.01); *C12N 2501/515* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 7,491,534 B2* | 2/2009 | Collas | C12N 5/0636 435/357 |
| 8,007,785 B2* | 8/2011 | Winqvist | A61K 35/26 424/93.71 |
| 8,545,838 B2* | 10/2013 | Epstein | A61K 47/48569 424/130.1 |
| 8,858,936 B2* | 10/2014 | Ferrara | A61P 37/06 424/130.1 |
| 2003/0138433 A1 | 7/2003 | Newell et al. | |
| 2005/0112141 A1* | 5/2005 | Terman | C07K 14/70503 424/192.1 |
| 2006/0269529 A1 | 11/2006 | Niederman et al. | |
| 2009/0202534 A1* | 8/2009 | Levin | C07K 16/2818 424/133.1 |
| 2010/0015161 A1* | 1/2010 | Winqvist | A61P 35/00 424/145.1 |
| 2013/0156730 A1 | 6/2013 | Mouritzen et al. | |
| 2014/0030806 A1 | 1/2014 | Dudley et al. | |
| 2015/0368360 A1 | 12/2015 | Liang et al. | |

FOREIGN PATENT DOCUMENTS

WO    2006/030442 A2    3/2006

OTHER PUBLICATIONS

McKee et al., (Frontiers in Bioscience, 2007,v.12, pp. 919-932.*
Dahl, et al., "Metinal Node—The First Lymph Node Draining a Metastasis—Contains Tumor-Reactive Lymphocytes" Annals of Surgical Oncology 15(5):1454-1463.
Dang, et al., "Tumor Antigen-Specific T-Cell Expansion is Greatly Facilitated by In Vivo Priming", Clin Cancer Res. 2007;13:1883-1891.
Okamoto, et al., "The Antitumor Effect of Tumor-Draining Lymph Node Cells Activated by Both Anti-CD3 Monoclonal Antibody and Activated B Cells As Costimulatory-Signal Providing Response", Cancer Immunology, Immunotherapy, 1995, vol. 40, Issue 3, pp. 173-181.
Vanneman, et al., "Combining Immunotherapy and Targeted Therapies in Cancer Treatment", Nature Reviews, Cancer, vol. 12, Apr. 2012, pp. 237-251.
Yoshizawa, et al., "Activation by Anti-CD3 of Tumor-Draining Lymph Node Cells for Specific Adoptive Immunotherapy", Cellular Immunology 134, pp. 473-479, (1991).
Brimnes, et al., Generation of autologous tumor-specific T cells for adoptive transfer based on vaccination, in vitro restimulation and CD3/CD28 dynabead-induced T cell expansion, Jan. 2012, pp. 1221-1231.
Rasmussen et al., "Ex vivo expansion protocol for hunlan tunlor specific T cells for adoptive T cell therapy", Journal of Immunological Methods, 2010, pp. 52-60.

* cited by examiner

*Primary Examiner* — Michail A Belyavskyi
(74) *Attorney, Agent, or Firm* — Tarolli, Sundheim, Covell & Tummino LLP

(57) ABSTRACT

A method of treating cancer in a subject includes contacting an enriched population of T-cells obtained from cancer or tumor draining lymph nodes ex-vivo with: an anti-CD3 antibody, an anti-CD28 antibody, and/or functional fragments thereof, and optionally a VEGF inhibitor and/or an IL-2 receptor agonist, at amounts effective to activate and expand the T-cells and administering the activated and expanded T-cells to the subject.

21 Claims, 14 Drawing Sheets

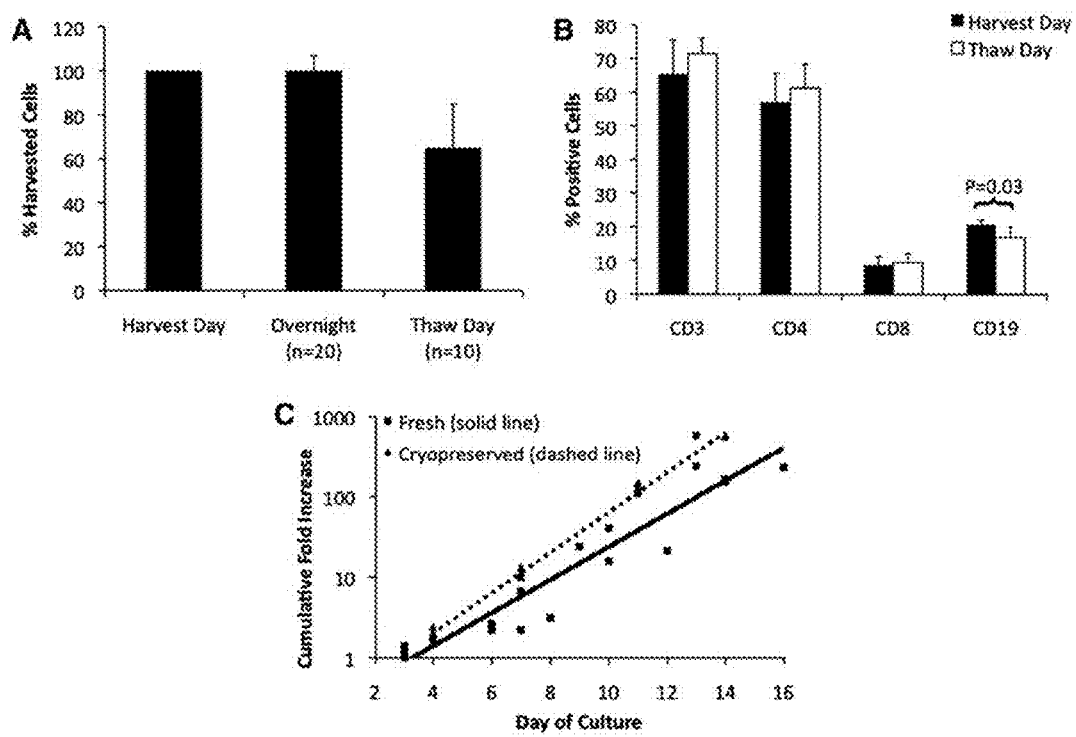
Figs. 2A-C
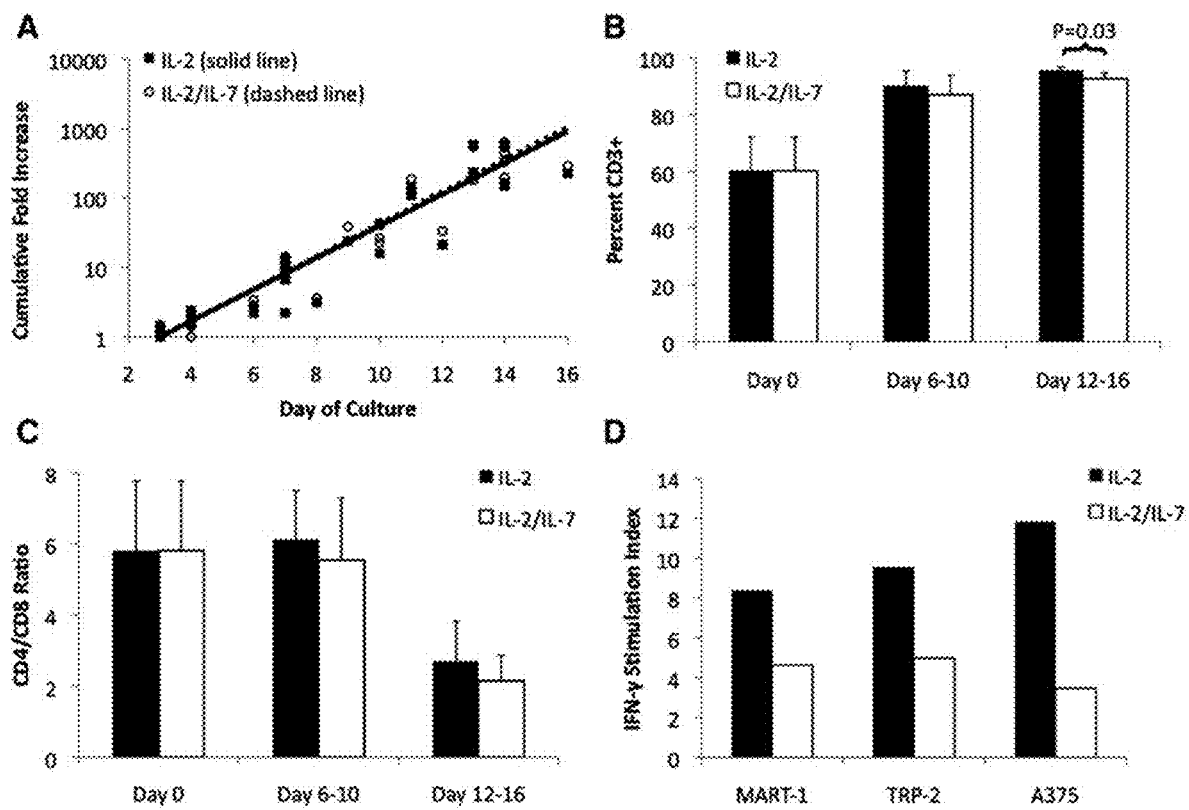
Figs. 3A-D

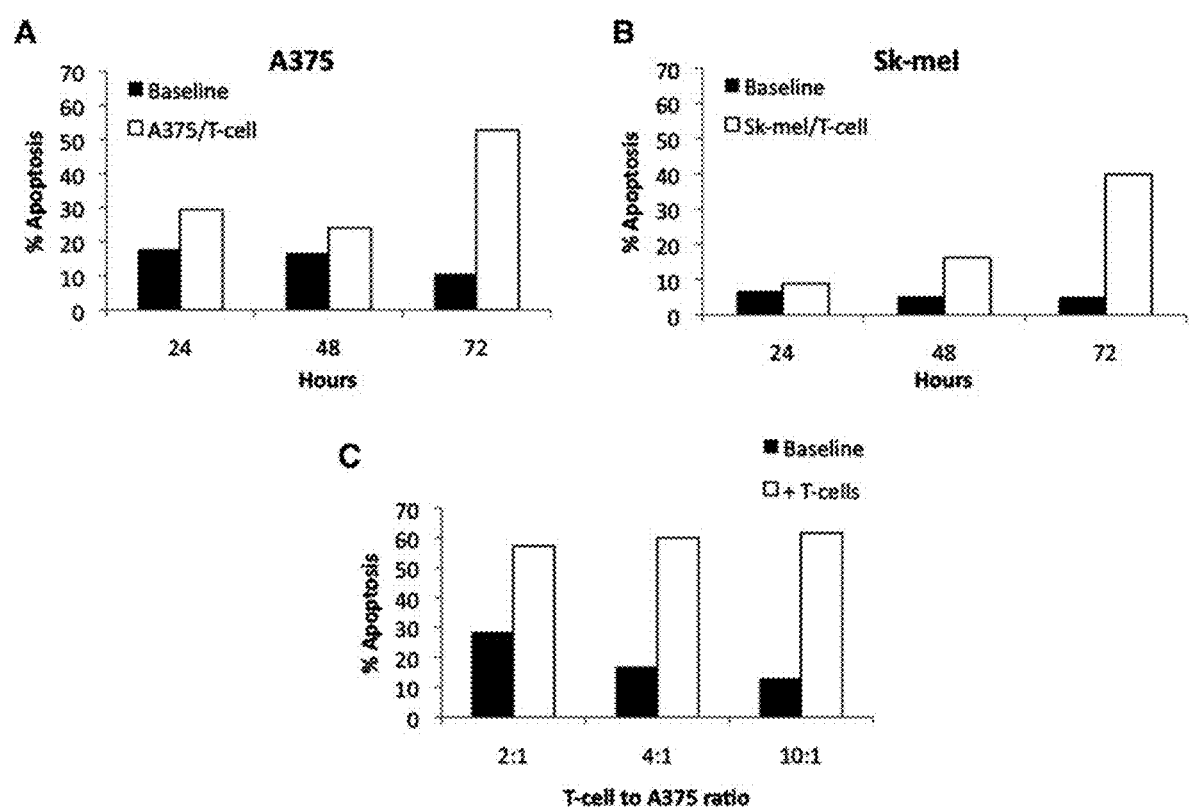
Figs. 4A-C

Figs. 7A-C

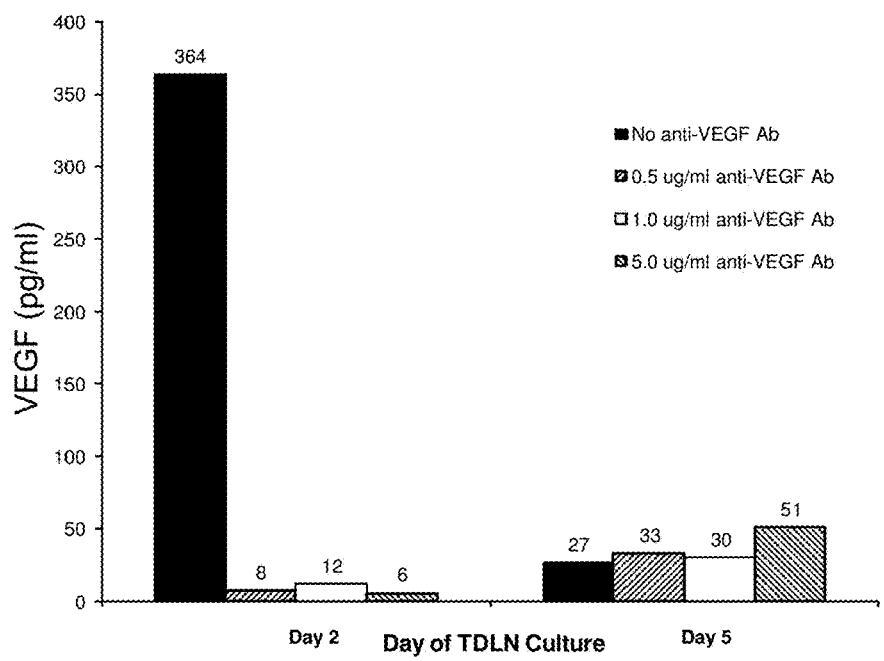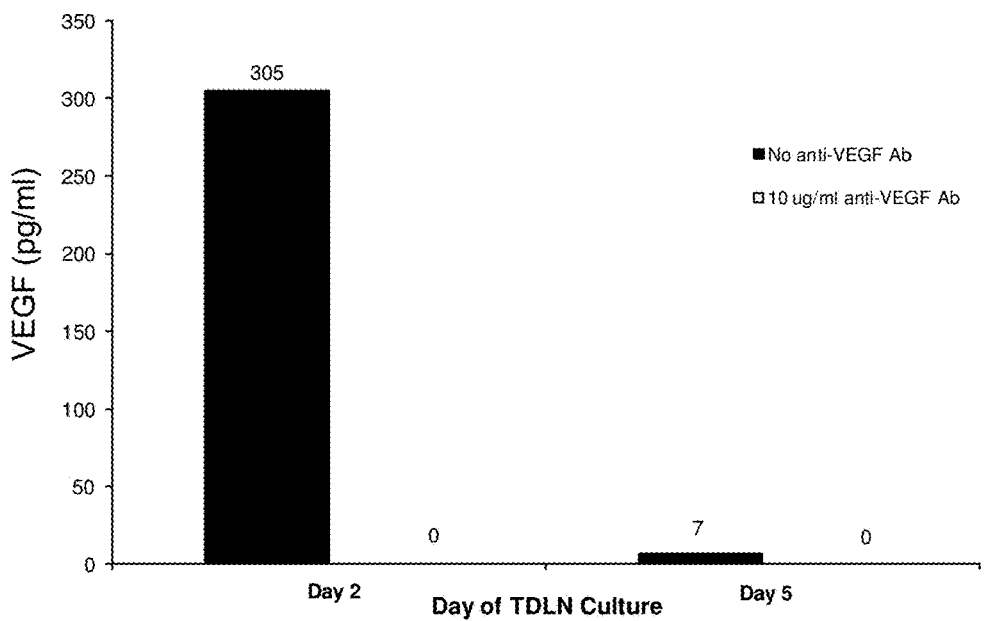
Figs. 10A-B

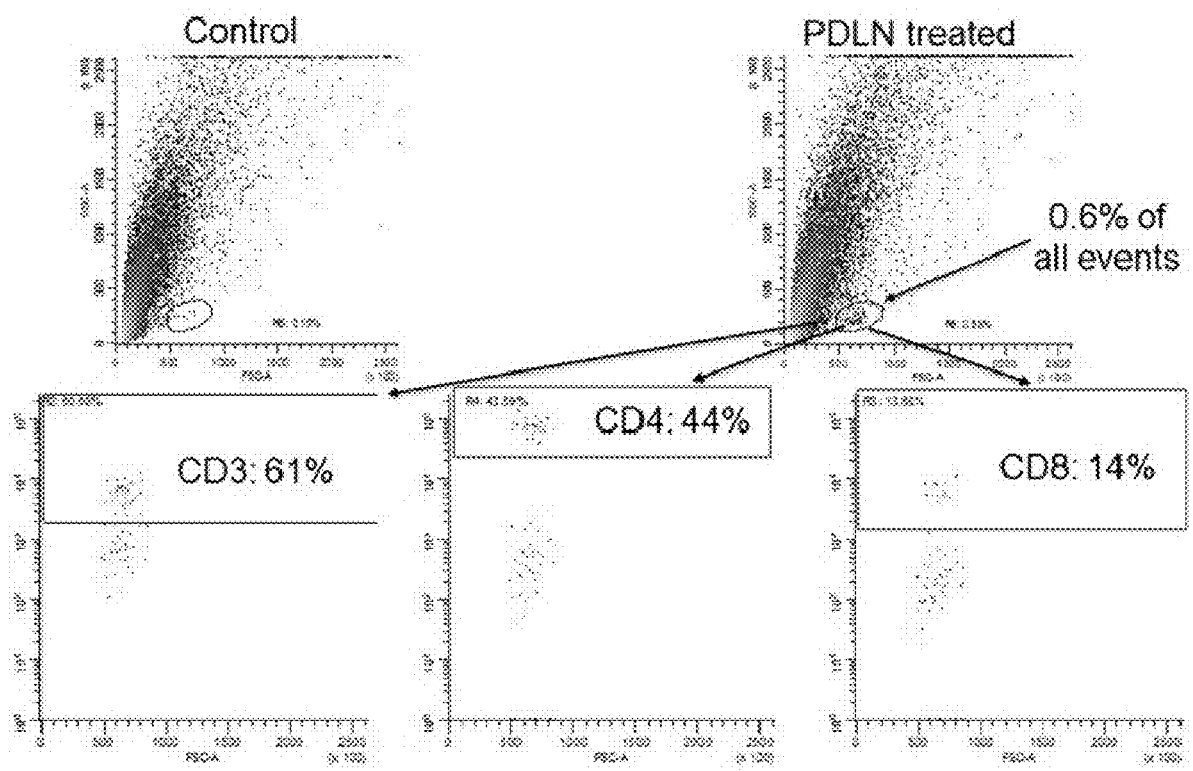
Fig. 18
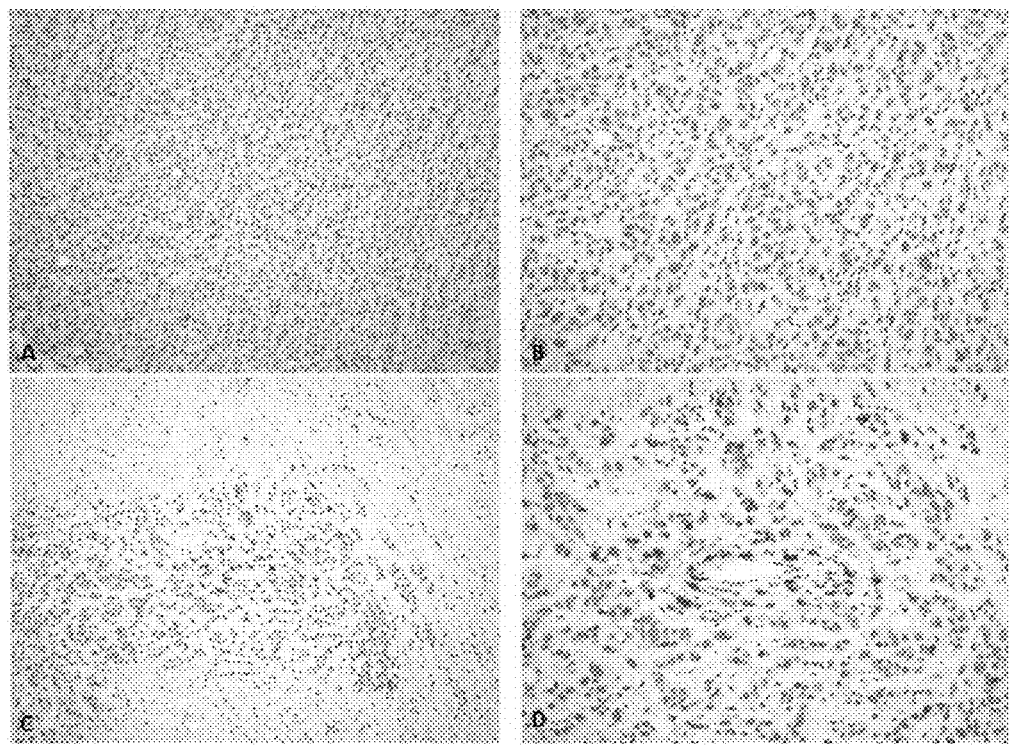
Figs. 19A-D

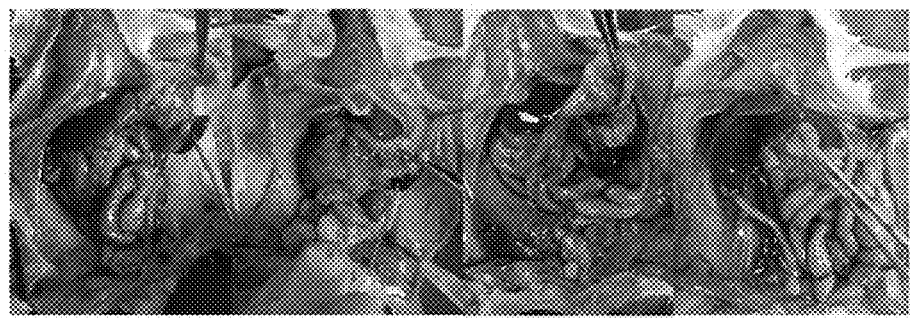
Fig. 22

METHOD OF GENERATING TUMOR-SPECIFIC T CELLS

RELATED APPLICATION

This application is a Continuation-in-Part of U.S. Ser. No. 14/205,069, filed Mar. 11, 2014, which claims priority to U.S. Provisional Application No. 61/776,352, filed Mar. 11, 2013, this application also claims priority from U.S. Provisional Application Ser. No. 62/560,943, filed Sep. 20, 2017, the subject matter of which is incorporated herein by reference in its entirety.

GOVERNMENT SUPPORT

This invention was made with government support under CA109115, K12 CACA07697-15 awarded by the National Institutes of Health and The National Cancer Institute. The government has certain rights in the invention.

TECHNICAL FIELD

The present invention relates to an improved method for expansion and activation of tumor-specific T-cells, in particular CD4+ helper and/or CD8+ T-cells.

BACKGROUND

The incidence of melanoma has been increasing steadily in both men and women for more than a decade. It is currently the fifth leading cause of cancer in men and the seventh in women. Immunotherapy using high-dose intravenous interleukin-2 (HD IL-2) has demonstrated modest response rates (~16%) in patients with metastatic disease, but many who undergo complete response will have durable responses beyond 10 years. HD IL-2 in combination with infusion of tumor-infiltrating lymphocytes (TILs) has increased the objective response rate to as high as 72% and durable complete response in up to 16% of patients with metastatic melanoma. These studies demonstrate proof-of-concept that immunotherapy can be efficacious in selected patients. However, there are significant limitations related to IL-2 toxicity and challenges surrounding the isolation and expansion of TILs in vitro that have limited the translation of this approach outside of a relatively few investigational sites. In addition, because many patients with stage III melanoma do not have significant volumes of tumor, TIL therapy is not feasible in this patient population.

SUMMARY

Embodiments described herein relate to a method for the expansion of tumor-specific T-cells that can be used to treat a subject suffering from cancer, such as a malignant cancer or metastasis of a malignant tumor (e.g., pancreatic cancer). The method includes obtaining an enriched population of T-cells from the subject suffering from cancer (pancreatic cancer). The enriched population of T-cells is then contacted ex-vivo with: (i) an anti-CD3 antibody, an anti-CD28 antibody, and/or functional fragments thereof, and optionally an IL-2 receptor agonist and/or a VEGF inhibitor at amounts effective to activate and expand the T-cells.

In some embodiments, the enriched population of T-cells is obtained from blood (e.g., peripheral blood of the tumor), a metastasis from a malignant tumor, or tumor draining lymph nodes of the subject.

The VEGF inhibitor can be selected from neutralizing monoclonal antibodies against VEGF or its receptor, small molecule tyrosine kinase inhibitors of VEGF receptors, soluble VEGF receptors, which act as decoy receptors for VEGF, and ribozymes, which specifically target VEGF mRNA or combinations thereof. In one example, the VEGF inhibitor can be a neutralizing monoclonal antibody against VEGF, such as be vacizumab.

In other embodiments, the activated and expanded T-cell population can be washed, and resuspended in a solution that does not include a VEGF inhibitor for infusion into the subject.

In some embodiments, the at least one substance having agonistic activity towards an IL-2 receptor can be IL-2, such as recombinant human IL-2.

In still other embodiments, the method can include obtaining the enriched population of T-cells by identifying lymph nodes draining the cancer in the subject and resecting one or more of the draining lymph nodes from the subject. The resected lymph nodes can be used to obtain an enriched population of T-cells, which is activated and expanded within a period of days, weeks, or months after resection.

In some embodiments, the resected lymph nodes can be cryopreserved after resection and then thawed prior to activation and expansion to obtain an enriched population of T-cells. This allows the enriched population of T-cells to be activated and expanded days, weeks, months, or years after resection, provides flexibility in the time at which the T-cells can be activated and expanded, and allows multiple infusions to be made over a prolonged period of time.

Advantageously, the resected lymph nodes are cultured with at least one IL-2 receptor agonist, such as IL-2, prior to cryopreservation to enhance the viability of the cryopreserved cells.

Other embodiments described herein relate to A method of treating pancreatic cancer in a subject. The method includes obtaining pancreatic cancer draining lymph node (PDLN) tissue from the subject. An enriched population of T-cells is then obtained from the PDLN tissue. The enriched population of T-cells is then contacted ex-vivo with an anti-CD3 antibody, an anti-CD28 antibody, and/or functional fragments thereof, and optionally a VEGF inhibitor and/or an IL-2 receptor agonist, at amounts effective to activate and expand the T-cells. The activated and expanded T-cells are then administered to the subject.

BRIEF DESCRIPTION OF THE DRAWINGS

FIGS. 2(A-C) illustrate graphs and a plot showing: (A) percentage of cells retained through the cryopreservation process; (B) phenotype of cells before and after cryopreservation; and (C) cumulative fold increase of T cells grown fresh from harvest or cultured after cryopreservation.

FIGS. 3(A-D) illustrate a plot and graphs showing: (A) growth curves for MDLN grown under 2 culture conditions; (B) percent of MDLN cells expressing CD3; (C) ratio of CD4+ T-cells to CD8+ T-cells; and (D) Antigen-specific IFN-γ production of the MDLN cells.

FIGS. 4(A-C) illustrate graphs showing: (A, B) % apoptosis at Day 14 of MDLN cultures incubated with 2 human melanoma tumor lines (A375 and Sk-mel, respectively) at a MDLN cell to tumor cell ratio of 2:1 for 24, 48, and 72 hours in MLDN cultures; and (C) % apoptosis of Day 14 MDLN cultures e incubated with human melanoma cell line (A375)

for 72 hours with increased MDLN cell-to-tumor cell ratios (2:1, 4:1, and 10:1). Apoptosis increased 28.9%, 43.1%, and 48.7% over baseline with an increasing MDLN cell ratio.

Figure 5:
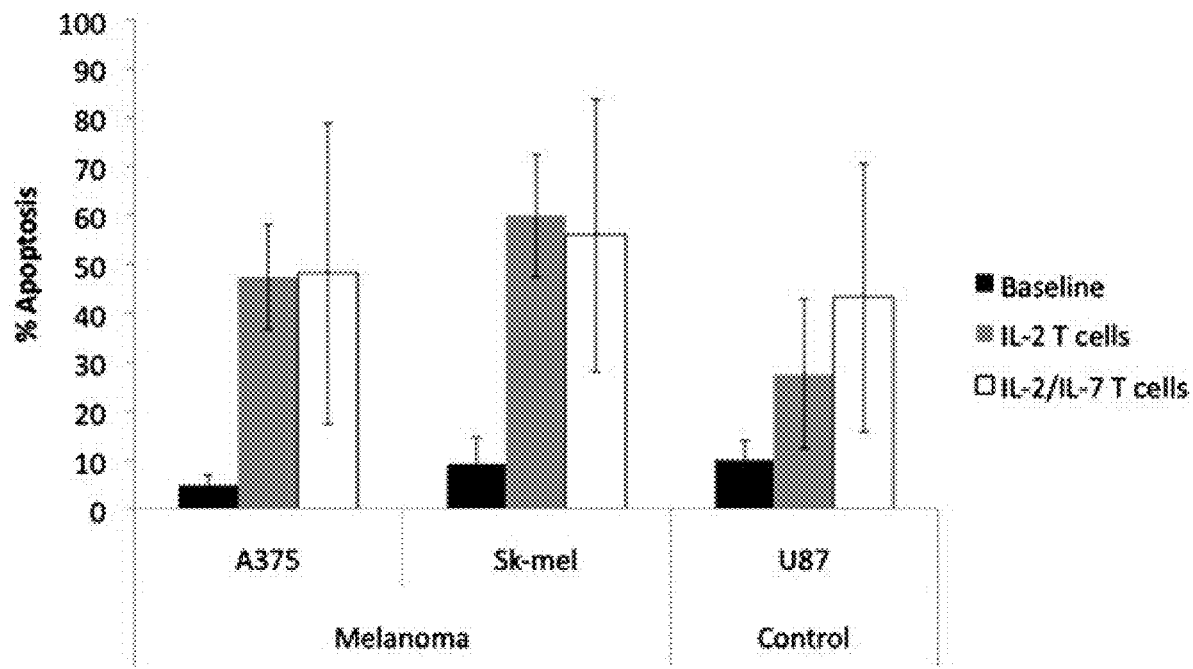

FIG. 5 illustrates a graph showing % apoptosis from MDLN generated by 2 culture conditions. Day 14 MDLN cells from IL-2 or IL-2/IL-7 cultures were incubated with 2 human melanoma lines (A375, Sk-mel) and 1 human brain cancer line (U87) at a ratio of 2:1 for 72 hours.

Figure 6:
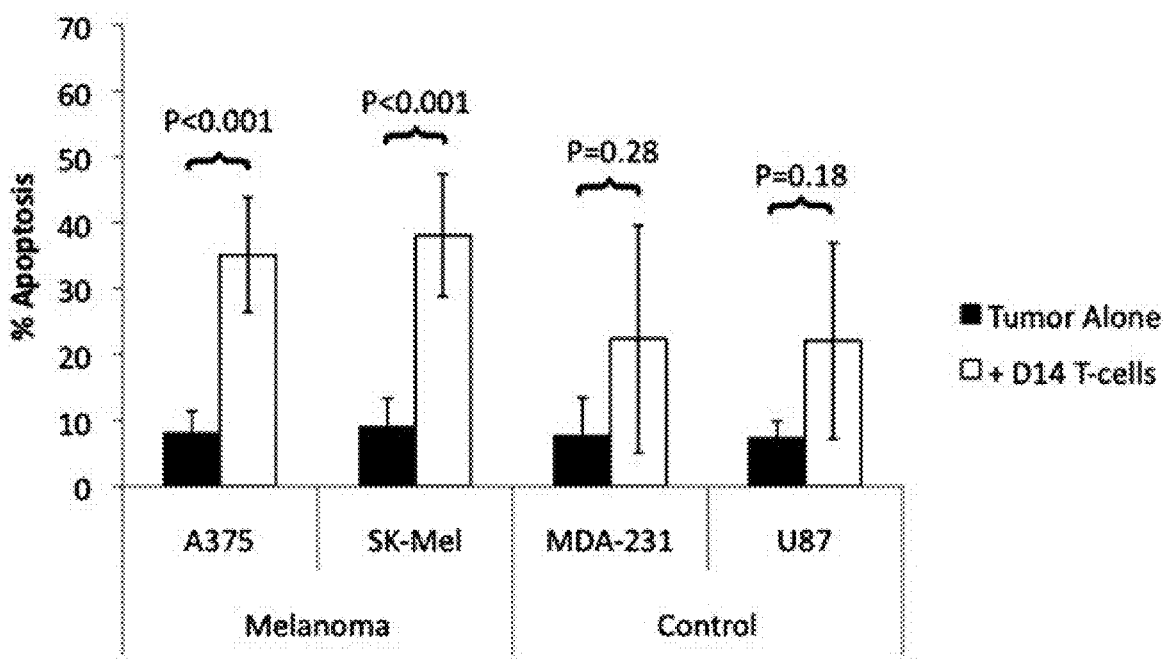

FIG. 6 illustrates graphs showing MDLN cultured in IL-2 resulted in melanoma-specific apoptosis. MDLN cells were incubated with 2 human melanoma cell lines (A375 and SK-Me1-28), 1 human breast cancer line (MDA-231), and 1 human brain cancer line (U-87).

Figure 7:
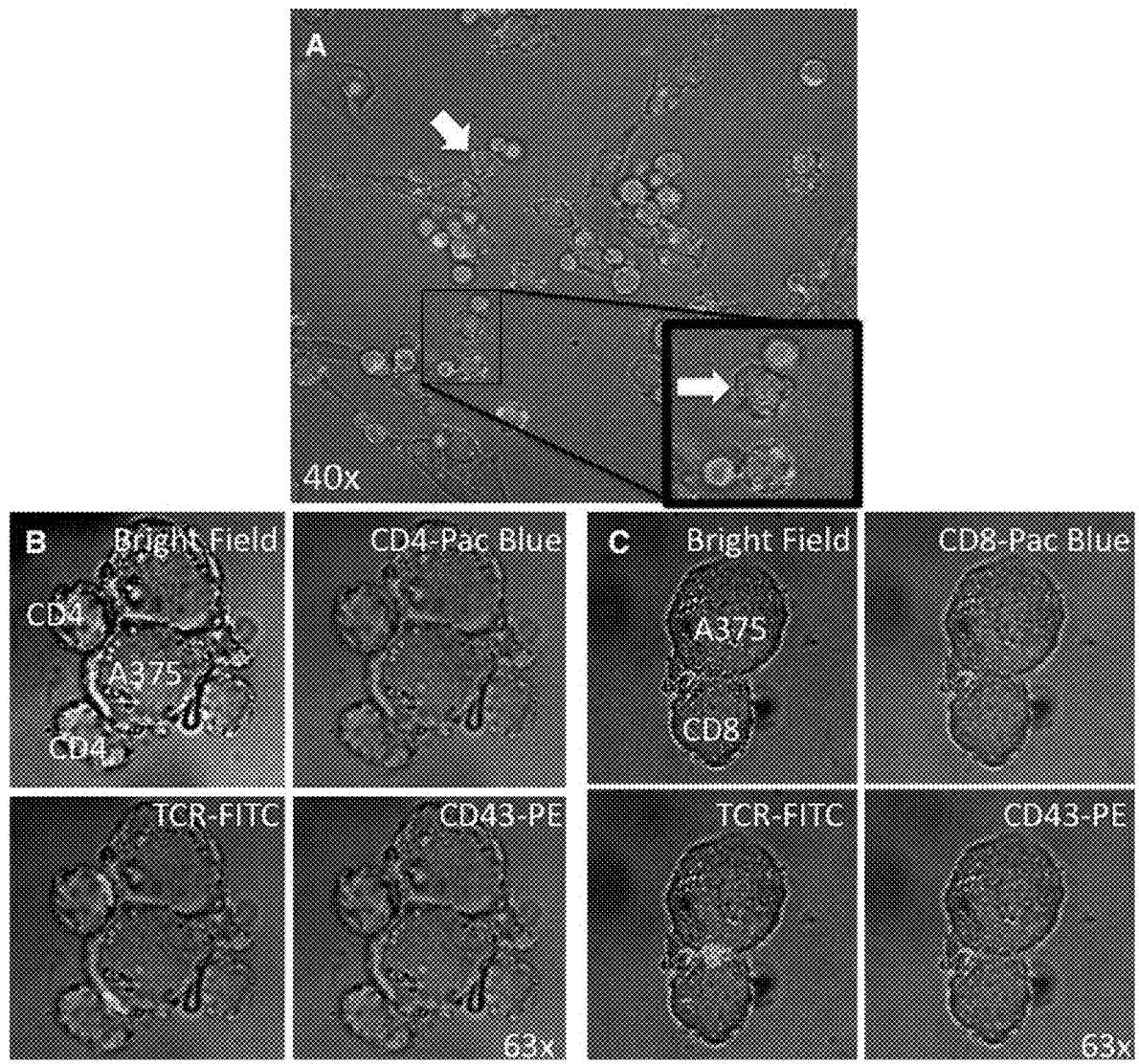

FIGS. 7(A-C) illustrate confocal fluorescent microscopy images showing: (A) apoptosis of A375 by CD3+ lymphocytes (340 magnification); and (B, C) formation of immunologic synapses between T cells and the melanoma tumor line (363 magnification).

Figure 8:
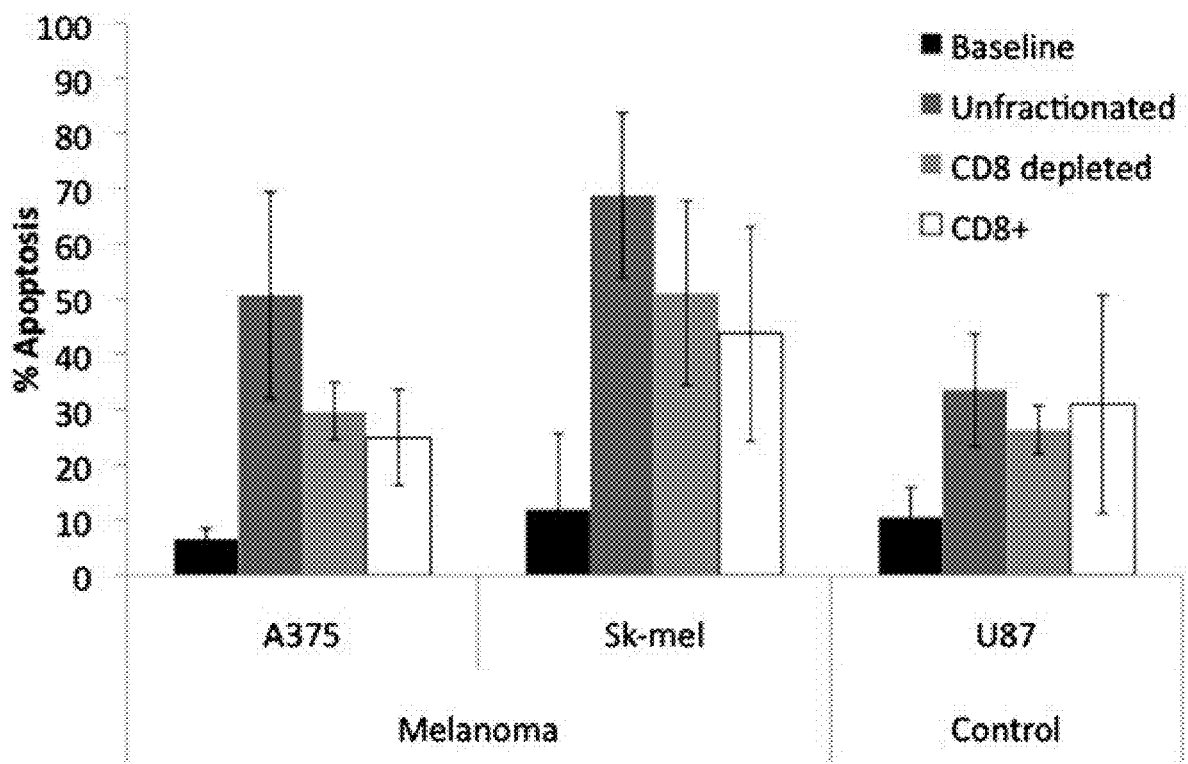

FIG. 8 illustrates a graph showing depletion of CD8 cells from MDLN. Day 14 MDLN cultures were labeled with anti-CD8 magnetic beads and depleted via magnetic column. Flowthrough cells were collected (CD8 depleted sample). The anti-CD8 cells were then washed from the column and collected (CD8+ sample). Apoptosis assays were performed as described, using A375, Sk-mel and U87 tumor cell lines. The ratio of CD8-depleted cells and CD8+ cells to tumor reflected the proportion of these respective samples in the unfractionated sample.

Figure 9:
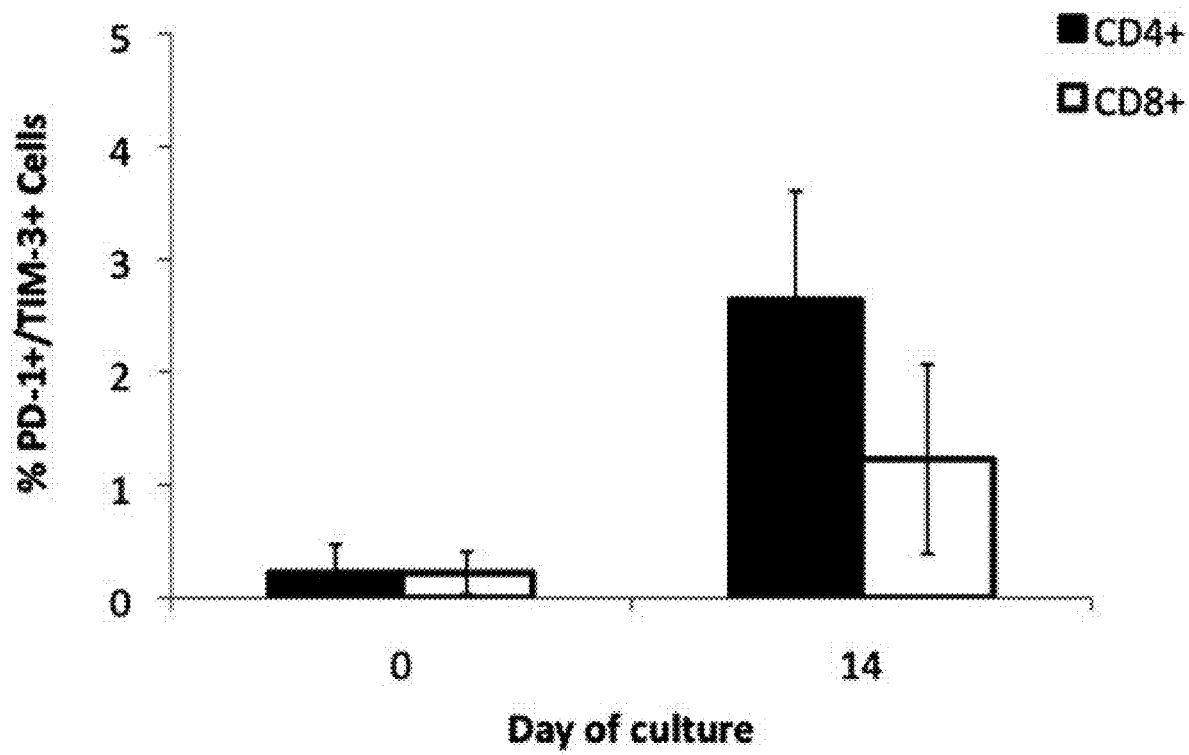

FIG. 9 illustrates a graph showing PD-1+/TIM-3+ lymphocytes at the beginning and end of culture. Cells were stained with antibodies to PD-1 and Tim-3, markers of T-cell exhaustion.

FIGS. 10(A-B) illustrate graphs showing the results of ELISA performed on supernatants collected from two separate experiments demonstrating the presence of high levels of soluble VEGF on Day 2 of TDLN culture in the absence of anti-VEGF mAb. VEGF was also present, but in lower concentrations, on Day 5 of culture. (A) Cells cultured with 5 µg/ml of antibody or less demonstrated near complete neutralization of VEGF on Day 2 but no discernible difference on Day 5. (B) Cells cultured with 10 µg/ml of antibody demonstrated complete neutralization of VEGF on Day 2 and Day 5.

Figure 11:
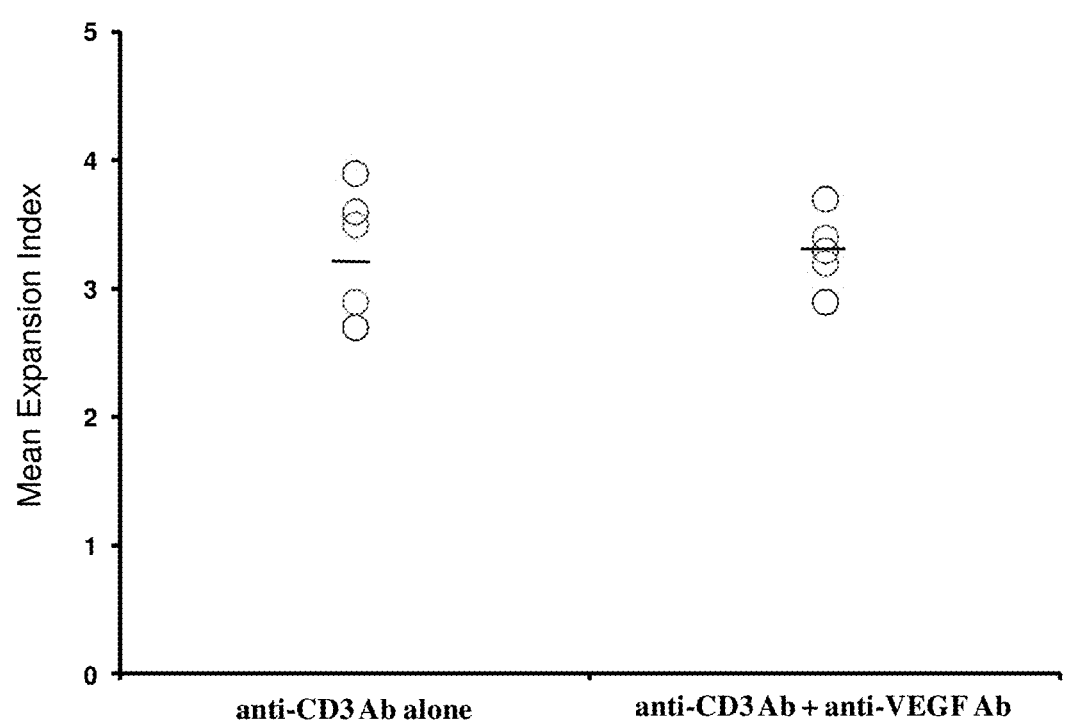

FIG. 11 illustrates a graph showing proliferation of 4T1 TDLN cells was not changed by the addition of anti-VEGF mAb in culture. Results from five separate experiments are shown. The mean expansion index following activation on immobilized anti-CD3 and incubation with IL-2 (4 U/ml) was 3.2× for cells cultured with anti-CD3 antibody alone (control) versus 3.3× for cells cultured with anti-CD3 and anti-VEGF mAb (10 µg/ml).

Figure 12:
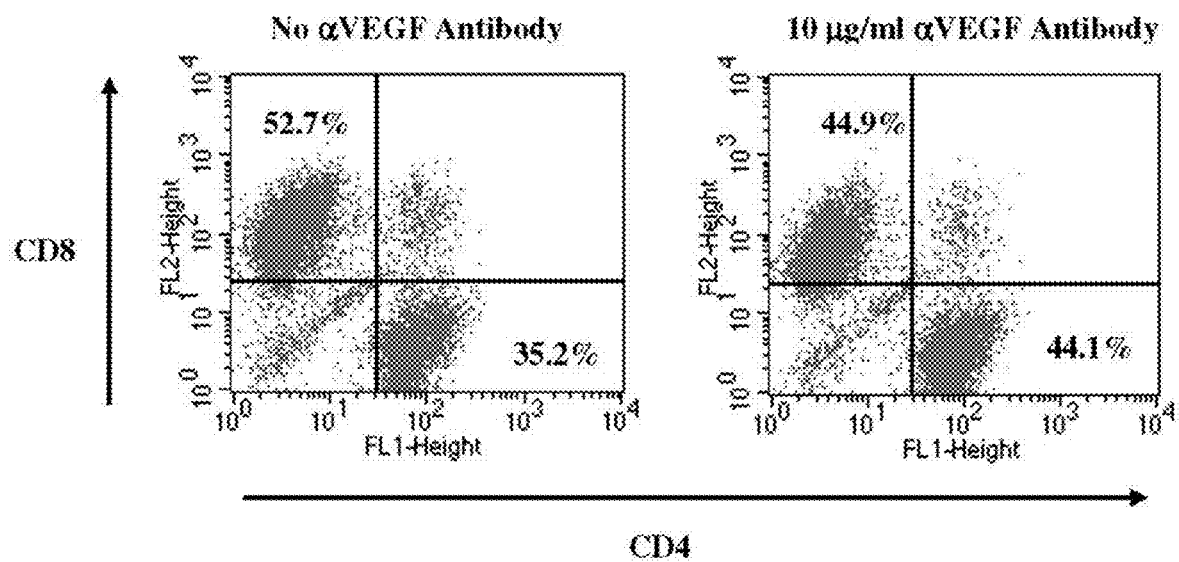

FIG. 12 illustrates scatter plots showing FACS analysis of T cells on Day 5 of culture demonstrate an increase in the CD4:CD8 ratio for cells cultured in the presence of anti-VEGF mAb (0.98) compared to cells cultured in the absence of anti-VEGF mAb (0.67). CD8 positive cells are shown in the upper left of the scatter plots, while CD4 positive cells are shown in the lower right.

Figure 13:
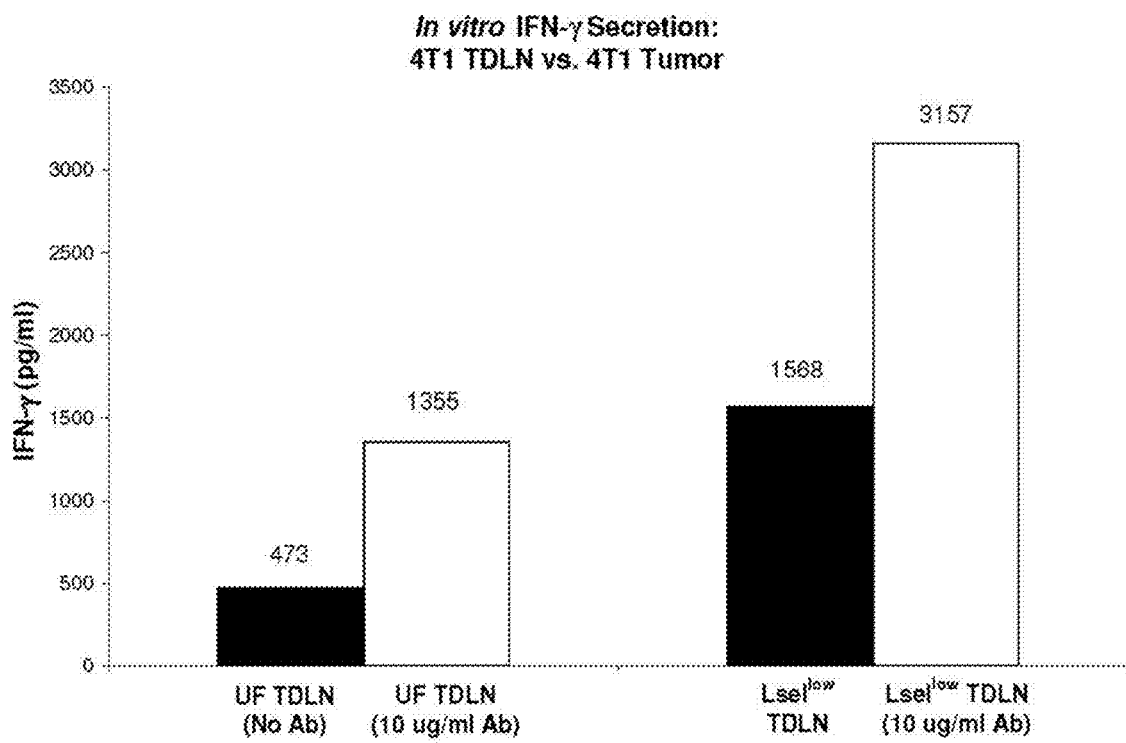

FIG. 13 illustrates a graph showing culture in the presence of anti-VEGF mAb resulted in an increase in tumor-specific IFN-γ secretion in vitro as demonstrated by ELISA. Both unfractionated (UF) and L-selectin$^{low}$ (Lsel$^{low}$) TDLN cells cultured in the presence of anti-VEGF mAb were shown to have increased IFN-γ secretion when incubated with fresh, irradiated 4T1 tumor cells as compared to similar cells cultured in the absence of anti-VEGF mAb.

Figure 14:
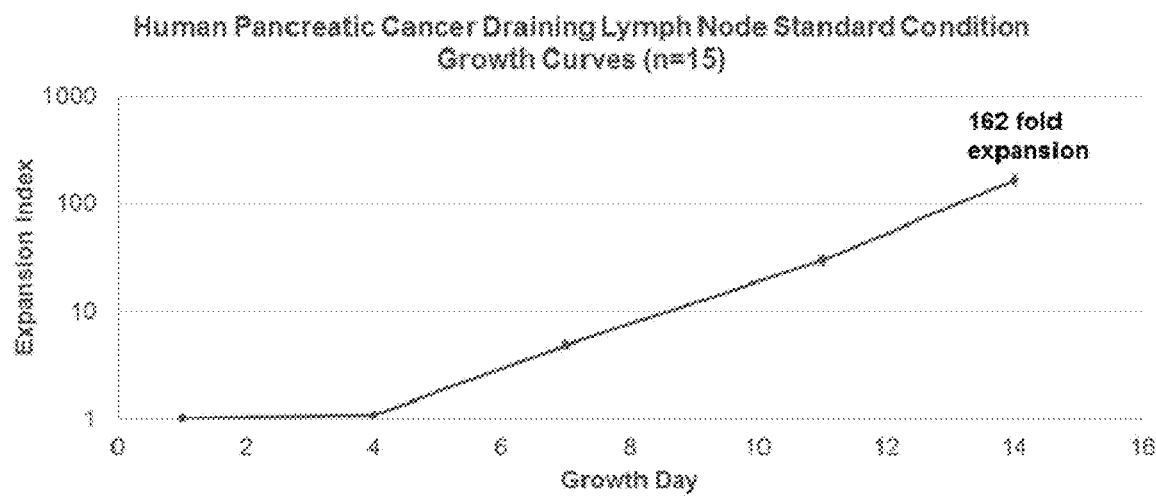

FIG. 14 illustrates a plot showing a human PDLN growth curve. The average growth of 15 PDLN cultures shows an average 162-fold expansion at day 14. Error bars indicate standard error of the mean.

Figure 15:
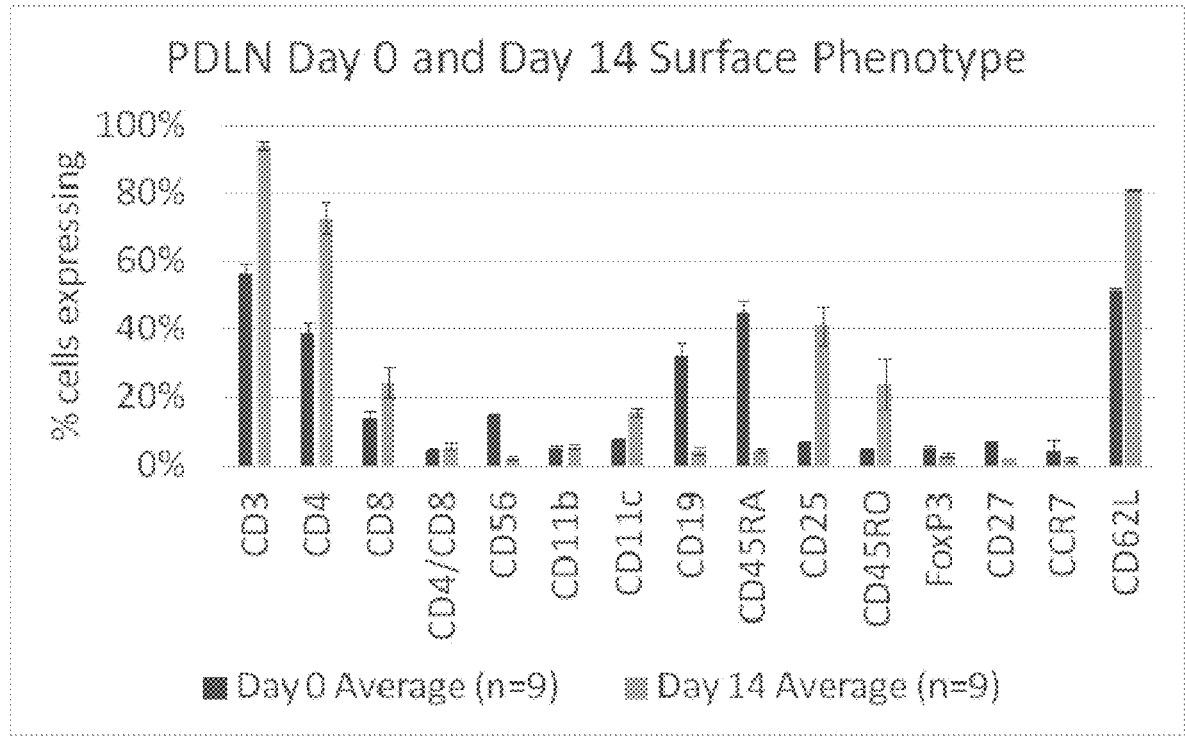

FIG. 15 illustrates a graph showing surface phenotypes of PDLN cells at day 0 compared to day 14. The average day 0 and day 14 surface phenotypes of 9 PDLN cultures is shown. Error bars indicate standard error of the mean. Note that by day 14, there are >90% CD3+ T-cells, with a CD4 to CD8 ratio of ~3:1. The decrease in CD45RA and increase in CD45RO indicates a shift towards activated T-cells.

Figure 16:
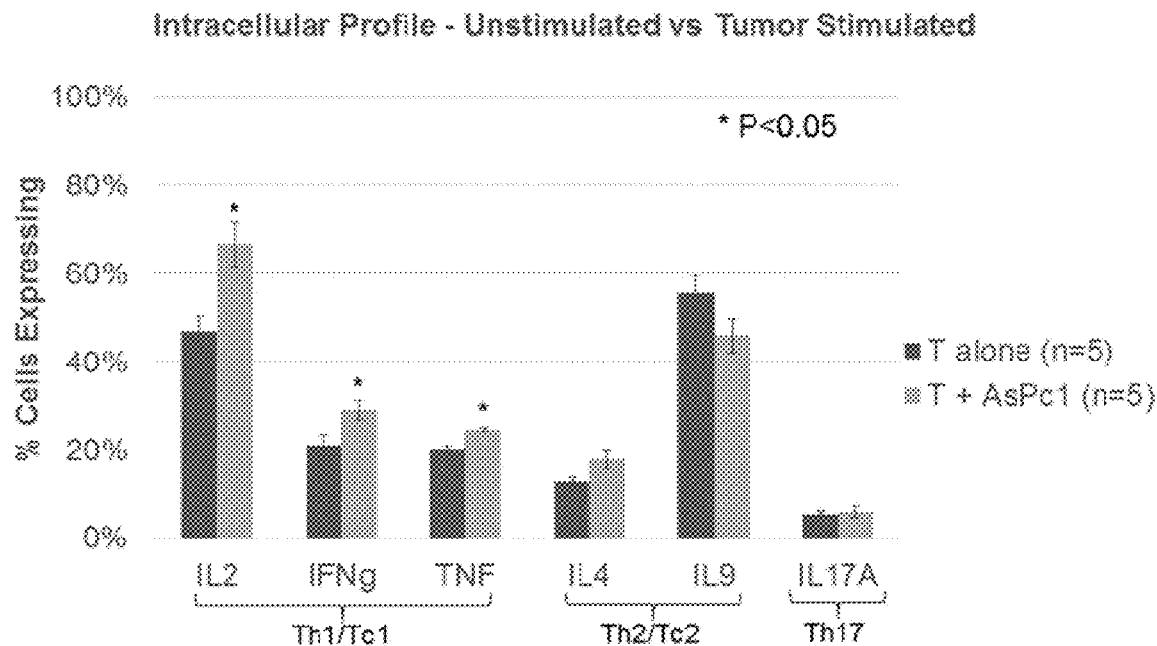

FIG. 16 illustrates a graph showing tumor stimulated cytokine profile of activated PDLN cells. The average intracellular cytokine production profiles from 5 cultures is shown. Error bars indicate standard error of the mean. Statistical significance was determined using a two-sided t-test with a p-value<0.05 as a cutoff. When T cells cultured alone are compared with T cells cultured in the presence of the human pancreatic cancer cell line AsPc1, there is a significant increase in the number of cells producing intracellular IL2, IFNγ, and TNF, indication a shift towards a Th1/Tc1 phenotype.

Figure 17:
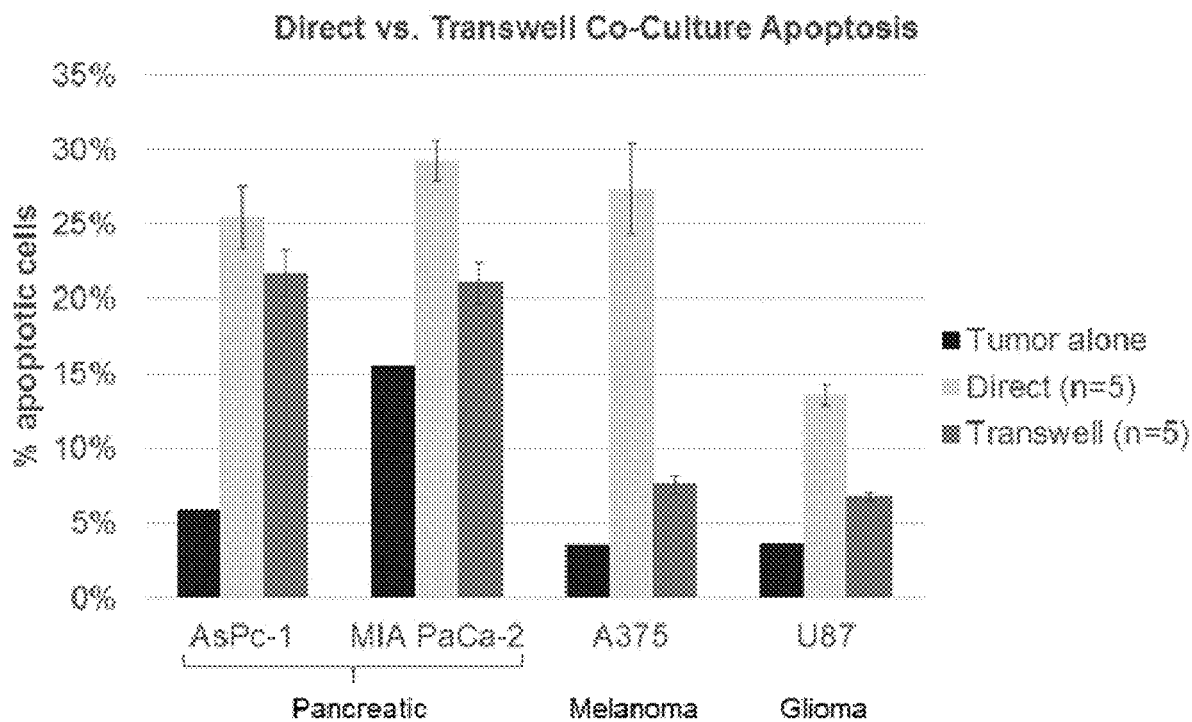

FIG. 17 illustrates a graph showing PDLN induced tumor apoptosis. The average tumor cell line apoptosis is shown. Error bars indicate standard error of the mean. When PDLN cells are directly co-cultured with various tumor cell lines (light grey bars), there is non-specific tumor apoptosis. However, when a Transwell plate is used to separate the tumor cells and PDLN cells (dark grey bars), a pattern of pancreatic cancer specific tumor apoptosis is observed as pancreatic cancer apoptosis remains high, while melanoma and glioma apoptosis is abrogated to near baseline levels.

FIG. 18 illustrates flow cytometry showing in vivo T cell trafficking to tumor. AsPc1 tumors were removed from NOD/SCID murine xenografts 3 weeks after AIT with PDLN cells were compared with control tumors. Note that in the PDLN treated mice, the tumor shows a distinct population representing 0.6% of all cell events which are 61% CD3+ T cells with a preserved CD4 to CD8 ratio of 3:1.

FIGS. 19(A-D) illustrates images showing in vivo PDLN T cell trafficking as seen by tumor IHC staining (CD8+=red, CD4+=brown). A) 10× view of AsPc-1 tumor in control mouse B) 20× view of AsPc-1 tumor in control mouse. C) 10× view of AsPc-1 tumor in mouse treated with 40×10$^6$ day 14 PDLN cells at 3 weeks. D) 20× view of AsPc-1 tumor in mouse treated with 40×10$^6$ day 14 PDLN cells at 3 weeks. Note the presence of both CD4 and CD8 cells clustered around tumor vasculature.

Figure 20:
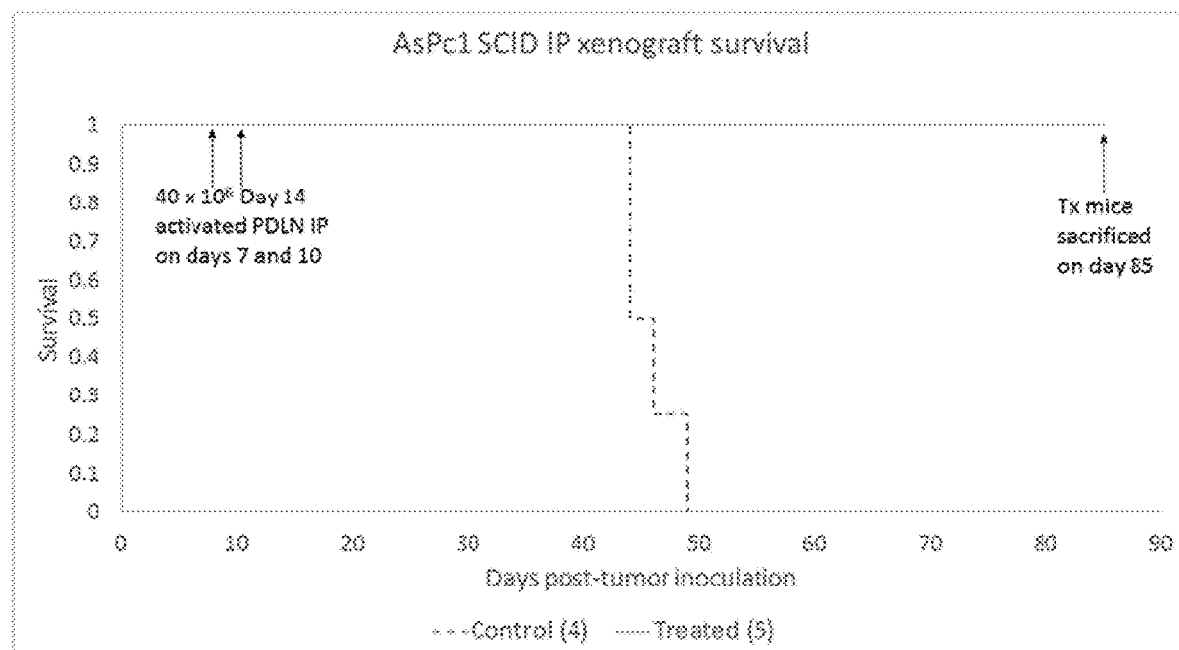

FIG. 20 illustrates a plot showing Kaplan-Meier survival curves comparing control to PDLN treated intraperitoneal AsPc1 bearing murine xenografts. All mice were inoculated with 1×10$^5$ AsPc1 cells on day 0. The control group (dashed line) received no intervention and all required euthanasia by day 49. The treatment group (solid line) received an infusion of 40×10$^6$ Day 14 activated PDLN cells on days 7 and 10 post-tumor inoculation. Treatment mice were asymptomatic by the end of the experiment at 85 days post-tumor inoculation.

Figure 21:
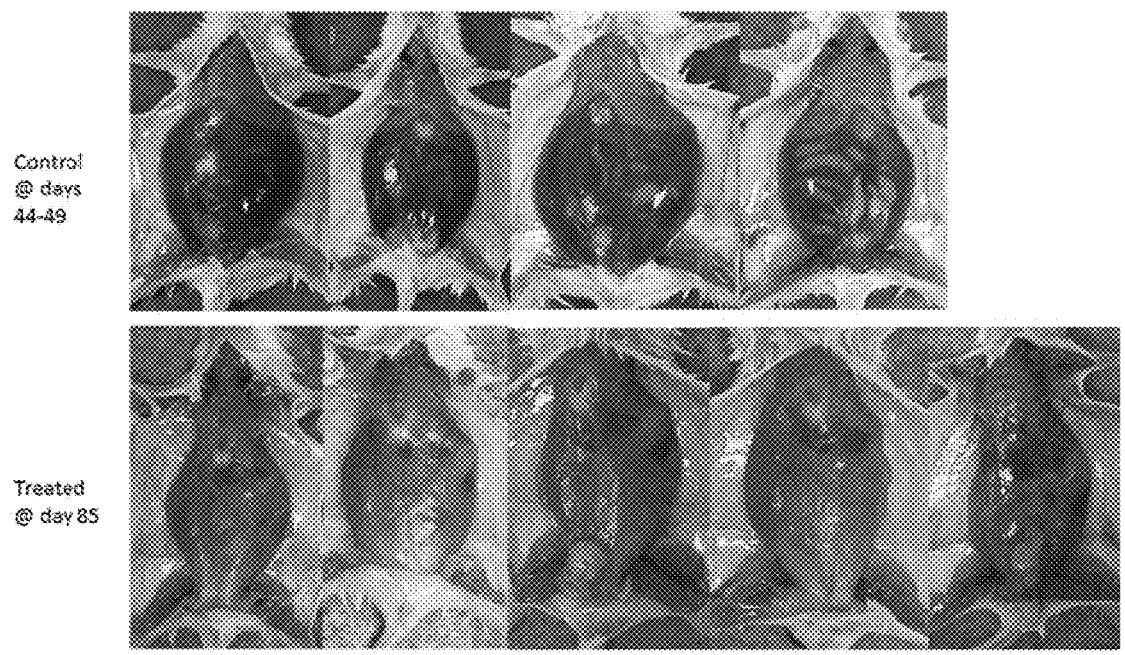

FIG. 21 illustrates images of AsPc1 intraperitoneal murine xenografts comparing control to PDLN treated mice. All mice were inoculated with 1×10$^5$ AsPc1 cells on day 0. The control group received no intervention and all required euthanasia between days 44 and 49. The treatment group (solid line) received an infusion of 40×10$^6$ Day 14 activated PDLN cells on days 7 and 10 post-tumor inoculation. Note the uniform presence of hemorrhagic ascites in the control group and the absence of it in the treated group.

FIG. 22 illustrates images of AsPc1 intraperitoneal murine xenografts comparing control to PDLN treated mice. All mice were inoculated with 1×10$^5$ AsPc1 cells on day 0. The control group received no intervention and all required euthanasia between days 44 and 49. The treatment group (solid line) received an infusion of 40×10$^6$ Day 14 activated PDLN cells on days 7 and 10 post-tumor inoculation. Note the uniform presence of carcinomatosis in the control group. The treatment group had isolated peritoneal deposits in 3 mice and no evidence of intraperitoneal disease in 2 mice.

DETAILED DESCRIPTION

The methods and techniques described herein are generally performed according to conventional methods well-known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane, Antibodies: A Laboratory Manual, Cold Spring Harbor Laboratory Press, Cold Spring Harbor, N.Y. (1990).

For clarification in understanding and ease in reference a list of terms used throughout the brief description section and the remainder of the application has been compiled here. Some of the terms are well known throughout the field and are defined here for clarity, while some of the terms are unique to this application and therefore have to be defined for proper understanding of the application.

"A" or "an" means herein one or more than one; at least one. Where the plural form is used herein, it generally includes the singular.

"Activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physicochemical process. The term "activated T cells" indicates T cells that are currently undergoing cell division, cytokine production, performance of reg or cytol effector functions, and/or has recently undergone the process of "activation."

"Antibody" refers to whole antibodies, e.g., of any isotype (IgG, IgA, IgM, IgE, etc.), and includes fragments thereof which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies. The term "diabodies" refers to dimeric scFvs. The components of diabodies typically have shorter peptide linkers than most scFvs and they show a preference for associating as dimers.

"Antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may comprise chains synthesized from engineered DNA sequences that have been modified by, for instance, substituting one amino acid for another to eliminate disulfide linkage sites. The fragment may also optionally be a multimolecular complex. A functional antibody fragment will typically comprise at least about 50 amino acids and more typically will comprise at least about 200 amino acids.

A "cell bank" is industry nomenclature for cells that have been grown and stored for future use. Cells may be stored in aliquots. They can be used directly out of storage or may be expanded after storage. This is a convenience so that there are "off the shelf" cells available for administration. The cells may already be stored in a pharmaceutically-acceptable excipient so they may be directly administered or they may be mixed with an appropriate excipient when they are released from storage. Cells may be frozen or otherwise stored in a form to preserve viability. In one embodiment of the invention, cell banks are created in which the cells have been selected for enhanced potency to achieve the effects described in this application. Following release from storage, and prior to administration to the subject, it may be preferable to again assay the cells for potency. This can be done using any of the assays, direct or indirect, described in this application or otherwise known in the art. Then cells having the desired potency can then be administered to the subject for treatment. Banks can be made using cells derived from the individual to be treated (from their lymph nodes).

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of and similar phrases using words of the root "comprise" are used herein as synonyms of "comprising" and have the same meaning.

"Comprised of" is a synonym of "comprising" (see above).

By the term "day 1 of the activation and expansion process" or e.g. "day 5 of the activation expansion process" is to be understood the following: The day on which the lymphocytes are harvested or thawed from cryopreservation is denoted day 0 (zero). Day 1 of the activation and expansion process is defined as the day where the activation and expansion is initiated by addition of at least one substance activating or expanding the harvested or thawed cryopreserved cells.

"Effective amount" generally means an amount which provides the desired local or systemic effect, e.g., effective to ameliorate undesirable effects of inflammation, including achieving the specific desired effects described in this application. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

An "enriched population" means a relative increase in numbers of a desired cell relative to one or more other cell types in vivo or in primary culture.

"Exogenously added," compounds such as growth factors, differentiation factors, and the like, in the context of cultures or conditioned media, refers to growth factors that are added to the cultures or media to supplement any compounds or growth factors that may already be present in the culture or media. For example, in some embodiments, cells cultures and or cell populations do not include an exogenously-added retinoid.

Use of the term "includes" is not intended to be limiting.

"Increase" or "increasing" means to induce a biological event entirely or to increase the degree of the event.

"Isolated" refers to a cell or cells which are not associated with one or more cells or one or more cellular components that are associated with the cell or cells in vivo. However, as used herein, the term "isolated" does not indicate the presence of only the cells described herein. Rather, the term "isolated" indicates that the cells described herein are removed from their natural tissue environment and are present at a higher concentration as compared to the normal tissue environment. Accordingly, an "isolated" cell population may further include cell types in addition to the cells described herein cells and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment (e.g., blood, lymph nodes).

When used in connection with cell cultures and/or cell populations, the term "portion" means any non-zero amount of the cell culture or cell population, which ranges from a single cell to the entirety of the cell culture or cells population. In preferred embodiments, the term "portion" means at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94% or at least 95% of the cell culture or cell population.

"Stimulation", as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex.

"Subject" means a vertebrate, such as a mammal, such as a human. Mammals include, but are not limited to, humans, dogs, cats, horses, cows, and pigs.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

"Lymphocyte" refers to any of the mononuclear non-phagocytic leukocytes found in the blood, lymph, and lymphoid tissues which are derived from lymphoid stem cells; they comprise the body's immunocytes and their precursors (e.g., T cells, B cells and Natural Killer (NK) cells).

"T cell" (i.e., T lymphocytes) refers to a lymphocyte that expresses a T cell receptor, CD3, and CD4 or CD8. The term includes several distinct T cell subpopulations (e.g., Cytotoxic T cells (CTLs or $T_C$), T regulatory ($T_{reg}$) cells, T helper ($T_H$) cells, $T_{H1}$ cells and $T_{H2}$ cells). The term "T cell" is further intended to include all cells within the T cell lineage, including thymocytes, immature T cells, mature T cells and the like, from a mammal (e.g., human or mouse).

"Tumor-specific T-lymphocytes" is intended to mean T-lymphocytes carrying a T cell receptor specific for and recognizing a tumor antigen.

"T helper cells" is intended to mean T-lymphocytes that promote adaptive immune responses when activated.

"Th1 cells" is intended to mean T helper cells that promote cell mediated immune responses when activated, using cytokines, such as IFN-gamma.

"Th2 cells" is intended to mean T helper cells promoting humoral immune responses when activated, using cytokines, such as IL-4.

"CD4+ helper T-cell" is intended to mean T-lymphocytes that express CD4 but not the transcription factor FoxP3.

"CD8+ T-cells" is intended to mean T-lymphocytes that express CD8.

"T regulatory cell" or "$T_{reg}$ cell" as used herein refers to a type of T cell that carries CD4 on its surface and is distinguished from $T_H$ cells by surface markers, such as CD25, associated with its stage of activation.

"Therapeutically effective amount" refers to the amount of an agent determined to produce any therapeutic response in a mammal. For example, effective anti-inflammatory therapeutic agents may prolong the survivability of the patient, and/or inhibit overt clinical symptoms. Thus, to "treat" means to deliver such an amount. Thus, treating can prevent or ameliorate any pathological symptoms of inflammation.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

"Validate" means to confirm. In the context of the invention, one confirms that a cell is an expressor with a desired potency. This is so that one can then use that cell (in treatment, banking, drug screening, etc.) with a reasonable expectation of efficacy. Accordingly, to validate means to confirm that the cells, having been originally found to have/established as having the desired activity, in fact, retain that activity. Thus, validation is a verification event in a two-event process involving the original determination and the follow-up determination. The second event is referred to herein as "validation."

Embodiments described herein relate to a method for the expansion of tumor-specific T-cells that can be used to treat a subject suffering from cancer, such as a malignant cancer or a cancer metastasis. It was found that T-cells obtained from a subject with a malignant cancer or cancer metastasis, such as melanoma, breast cancer, pancreatic cancer, lung cancer, and colorectal cancer, when activated in the presence of a VEGF inhibitor, such as a neutralizing anti-VEGF antibody, can generate Th1 interferon-γ secreting CD4$^+$ cells with enhanced therapeutic efficacy against established tumors of the subject.

The expansion method can be used for obtaining a high number of tumor-specific CD4+ helper and/or CD8+ T-cells in a relatively short time span (e.g., within two weeks). In some embodiments, the method can include obtaining an enriched population of T-cells from a subject suffering from cancer and then contacting the enriched population of T-cells ex-vivo with: (i) an anti-CD3 antibody, an anti-CD28 antibody, and/or functional fragments thereof, and (ii) a VEGF inhibitor at amounts effective to activate and expand the T-cells.

In some embodiments, the enriched population of T-cells can be a mixture of lymphocytes obtained from lymph nodes draining a tumor and/or a cancer metastasis of the subject being treated. The lymph nodes can be identified during surgery, e.g., by injection of a lymph node locator, such as a tracer substance, around or into the tumor or metastasis. The lymph node locator, e.g., the tracer substance, can be transported in the lymph capillaries and accumulate in the lymph node(s), thus identifying the tumor or metastasis draining lymph node(s). The lymph nodes that receive drainage from a tumor are a potential rich source for naturally tumor-specific CD4+ helper and/or CD8+ T-cells for ex vivo or in vitro expansion. Such nodes may contain a substantial amount of T-cells that have been sensitized towards tumor-antigens and undergone in vivo expansion in the lymph nodes. The identified lymph nodes can be resected using known surgical techniques to obtain an enriched population of T-cells, which are activated and expanded within a period of days, weeks, or months after resection.

An alternative source of T-cells may be the blood of a subject suffering from cancer, such as, e.g., peripheral blood. The subject may be an untreated patient that has had the disease for an extended time period or a treated patient that includes peripheral T-cells sensitized towards a tumor. Other sources of T-cells include bone marrow, spleen tissue, and tumors of the subject.

While the T-cells to be expanded in culture can be obtained from the subject to be treated, i.e., the resulting specific tumor-specific T-cells for administering may be autologous; in other embodiments, the T-cells can be obtained from a source other than the subject to be treated, such as another subject suffering from a cancer. In such case, the recipient and the expanded tumor-specific T-cells can be immunologically compatible (or the recipient is otherwise made immuno-tolerant of the expanded tumor-specific T-lymphocytes).

In some embodiments, the resected lymph nodes can be cryopreserved after resection and then thawed prior to expansion to obtain an enriched population of T-cells. This allows the enriched population of T-cells to be activated and expanded days, weeks, months, or years after resection, provides flexibility in the time at which the T-cells can be activated and expanded, and allow multiple infusions to be made over a prolonged period of time.

Figure 1:
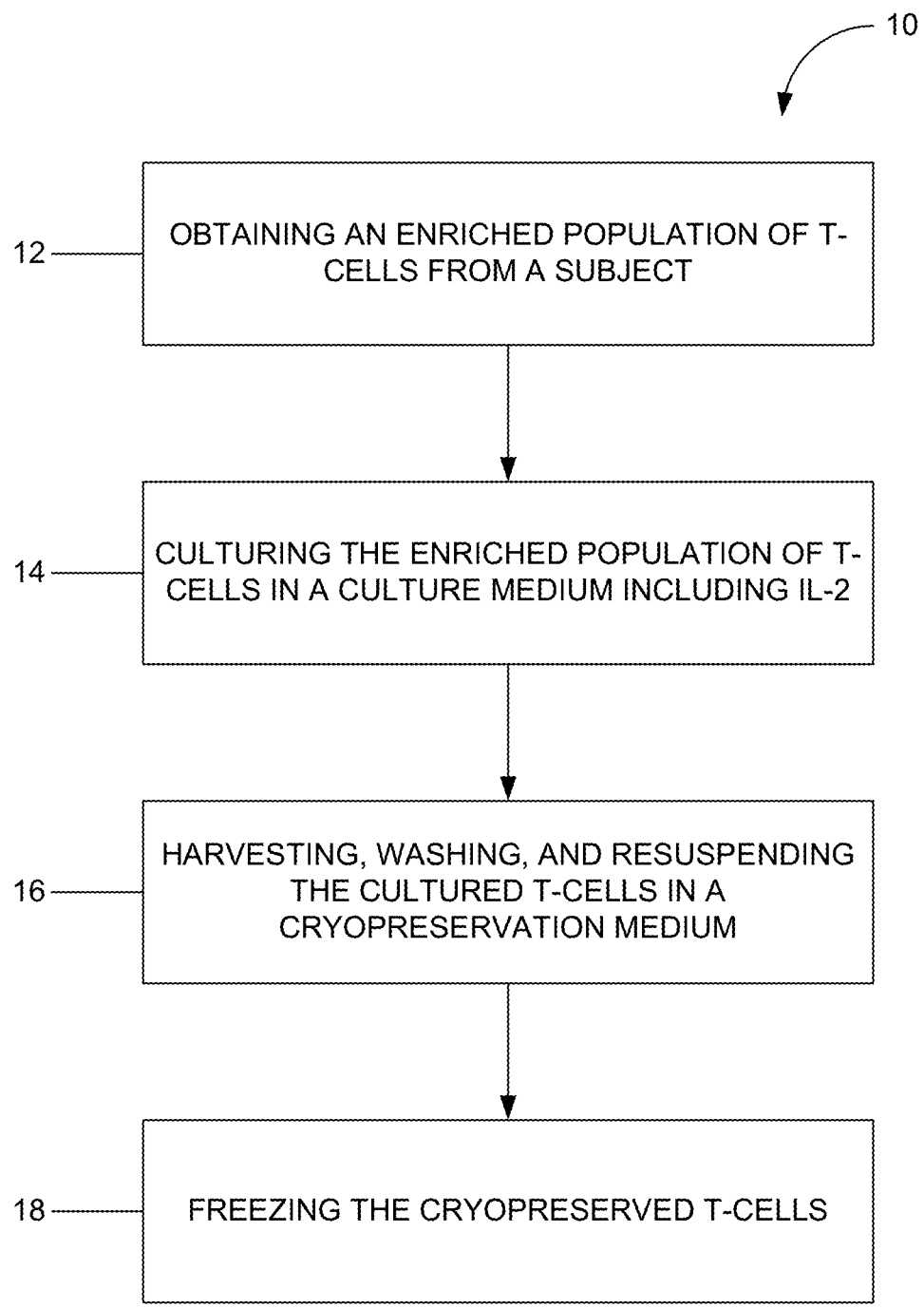
FIG. 1 illustrates a flow chart showing a method of cryopreserving T-cells in accordance with an embodiment described herein.

FIG. 1 is a flow diagram illustrating an example of a method 10 of cryopreserving the T-cells obtained from the subject with cancer. The method 10 at step 12 includes first obtaining an enriched population of T-cells from the subject. As discussed previously, the enriched population of T-cells can be obtained by identifying lymph nodes draining a tumor or cancer metastasis and resecting the lymph nodes.

A portion of the resected lymph nodes can be placed into a storage vessel containing, for example, complete media and 5% pooled human AB serum. The lymph node pieces can be minced into small pieces, such as pieces having a diameter no more than 5 mm, and then lymph node cells can be dispersed into a single cell suspension.

At step 14, the lymph node cells in suspension can then be cultured in a culture medium at a density of at least $10^5$ cells/ml, for example, at a density of about $10^6$ cells/ml, for about 12 to about 36 hours. The culture medium can include human AB serum and with at least one substance having agonistic activity towards an IL-2 receptor. The function of such substances is to stimulate T-lymphocytes via the IL-2 receptor to promote cell division of T-lymphocytes thereby preventing cell death.

The at least one substance having agonistic activity towards an IL-2 receptor can be human recombinant IL-2. Advantageously, it was found that culturing the enriched population of T-cells from the lymph nodes with IL-2 prior to freezing enhanced the viability of the cells once frozen, stored, and thawed.

The IL-2 can be added to the culture medium at a concentration from about 50 IU/ml culture medium to about 700 IU/ml culture medium, such as, e.g., from about 50 IU/ml culture medium to about 600 IU/ml culture medium, from about 50 IU/ml culture medium to about 500 IU/ml culture medium, from about 50 IU/ml culture medium to about 400 IU/ml culture medium, from about 50 IU/ml culture medium to about 300 IU/ml culture medium and from about 50 IU/ml culture medium to about 200 IU/ml culture medium.

Following culturing at step 16, the lymph node cells can be harvested from the culture medium, washed, and suspended in cryopreservation solution. The cryopreservation solution can be provided in a cryopreserve bag and include, by volume, about 5% to about 25% DMSO, and about 75% to about 95% human serum. In some embodiments about $10^6$ cells/ml to about $20^6$ cells/ml can be provided in the cryopreserve bags.

At step 18, the cryopreserved cells can then be frozen, stored in liquid nitrogen in a cell bank, and then thawed for later use.

The enriched population of T-cells, such as an enriched population of T-cells obtained from draining lymph nodes, can be activated and expanded by culturing the enriched population of T-cells in a culture medium that includes: (i) an anti-CD3 antibody, an anti-CD28 antibody, and/or functional fragments thereof, and (ii) a VEGF inhibitor at amounts effective to activate and expand the T-cells.

The anti-CD3 antibody, anti-CD28 antibody, and/or functional fragments thereof may be soluble in the culture medium or immobilized on a support, such as a bead, that is provided in the culture medium. For example, the anti-CD3 antibody, anti-CD28 antibody, and/or functional fragments thereof can be provided in the culture medium in the form of DYNABEADS with anti-CD3 and anti-CD28 antibodies on the surface of the DYNABEADS. Use of DYNABEADS CD3/CD28 can provide cultured T-cells with activation signals and can also be used for separation from possible tumor cells in the culture. DYNABEADS CD3/CD28 will bind to T-cells will further promote clonal expansion.

The anti-CD3 antibody, anti-CD28 antibody, and/or functional fragments thereof can be provided in the culture medium with the enriched population of the T-cells at an amount effective to activate the enriched population of T-cells. In some embodiments, the amount of anti-CD3 antibody, anti-CD28 antibody, and/or functional fragments thereof can be provided in the culture medium in the form of anti-CD3/anti-CD 28 antibodies at an amount of about 5 $\mu l/10^6$ cells to about 50 $\mu l/10^6$ cells, e.g., about 25 $\mu l/10^6$ cells.

The VEGF inhibitor that is provided in the culture medium can include proteins, monoclonal antibodies, antibody derivatives, or small molecules that inhibit activation of VEGF receptor or tyrosine kinases by VEGF. Examples of VEGF inhibitors that are monoclonal antibodies or antibody derivatives are bevacizumab (AVASTIN, used for medical indications in metastatic colorectal cancer, non-small cell lung cancer and metastatic breast cancer) and ranibizumab (LUCENTIS). Examples of VEGF inhibitor that are small molecule inhibitors are sunitinib (SUTENT), sorafenib (NEXAVAR), N-Methyl-2-[[3-[(E)-2-pyridin-2-ylethenyl]-1H-indazol-6-yl]sulfanyl]benza-mide (AXITINIB), and 5-[[4-[2,3-Dimethyl-2H-indazol-6-yl)(methyl)amino]pyrimidin-2-yl]amino]-2-methylbenzene-sul- fonamide (PAZOPANIB).

In some embodiments, the VEGF inhibitor can be provided in the culture medium at an amount effective to neutralize soluble endogenous VEGF secreted by the cultured lymph node cells. This amount will vary depending on the VEGF inhibitor added to the culture medium and the number of lymph node cells provided in the culture medium. In one example, $25 \times 10^6$ lymph nodes cells can be provided in the culture medium with about 0.1 µg/ml to about 100 µg/ml, about 1 µg/ml to about 50 µg/ml, or about 5 µg/ml to about 25 µg/ml of an anti-VEGF monoclonal antibody, such as bevacizumab, to neutralize endogenous VEGF secreted by the cells.

In some embodiments, the culture medium that is used for expansion and activation of the T-cells can include at least one substance having agonistic activity to IL-2 receptors to reduce lymphocyte apoptosis and to increase the population of CD4 positive helper tumor-specific T-lymphocytes. Examples of such substances include proteins, polypeptides, peptides, antibodies, affibodies, and fragments thereof, fusion proteins, synthetic and/or organic molecules, such as, e.g., small molecules, and natural ligands. In one example, the substance is the natural ligand of the IL-2 receptor, namely IL-2.

The IL-2 can be added to the culture medium at a concentration from about 50 IU/ml culture medium to about 700 IU/ml culture medium, such as from about 50 IU/ml culture medium to about 600 IU/ml culture medium, from about 50 IU/ml culture medium to about 500 IU/ml culture medium, from about 50 IU/ml culture medium to about 400 IU/ml culture medium, from about 50 IU/ml culture medium to about 300 IU/ml culture medium and from about 50 IU/ml culture medium to about 200 IU/ml culture medium.

The culture medium for activation and expansion of the T-cells can also include standard media, such as AIM-V medium, RPMI 1640, DMEM and MEM. Other media may also be used and can optionally include a blend of amino acids, steroids, vitamins, growth factors, cytokines and minerals.

The lymph node cells provided in the culture medium can be incubated at typical cell expansion temperatures and atmosphere, e.g., at about 37° C. and about 5% $CO_2$, for about 3 to about 5 days to expand and activate the T-cells. During expansion, the cells may be split into several culture vessels in order to maintain a suitable cell density in the cultures. The density of the T-cells in the expansion can be about 2.5 to about $5 \times 10^5$ cells/ml of culture medium. For example, cells and supernatant can be diluted ("split") with complete media containing about 100 IU/ml IL-2 to achieve a final cell concentration of $2.5-5 \times 10^5$ cells/ml depending upon how well the cells are expanding. During cell number expansion, further cell dilutions/splits can occur on days 6-7 and 10-11 depending upon cell density.

In some embodiments, one or more substances that promote the development of Th1 type T-cells can also be provided in the culture medium during expansion and activation of the T-cells. Examples of such substances are substances having agonistic activity towards the IL-7, IL-12, IL-15 and/or IL-21 receptor. More specific, the substances may be agonists for the IL-7, IL-12, IL-15 and/or IL-21 receptor. Examples of such agonists include proteins, polypeptides, peptides, antibodies, affibodies, and fragments thereof, fusion proteins, synthetic and/or organic molecules, such as, e.g., small molecules, and natural ligands. In a specific embodiment the substances are the natural ligands of the IL-7, IL-12, IL-15 and/or IL-21 receptor, respectively, such as IL-7, IL-12, IL-15 and/or IL-21.

The IL-7, IL-12, IL-15 and/or IL-21 can provided in the culture medium at concentration of each of these substances within the range from about 150 IU/ml culture medium to about 300 IU/ml culture medium, such as, e.g., 250 IU/ml culture medium.

The tumor-specific T-cells can be harvested at some point, leading to the termination of the activation and expansion step. In some embodiments, the tumor-specific T-cells can be harvested between days 13-16 to achieve as close to the final total number of cells that are required for infusion and treatment of the subject.

The identity of the final infusion product is an activated tumor-specific T cell product, and the validation of the identity can be performed using FACS analysis of T cell subsets. The primary measure of identity will be a proportion of CD3+ cells, which are present in the total cell population. A variety of surface markers in addition to CD3 can be analyzed and include: CD8/CD45RO, CD4/CD45RO, CD8/CD27- and CD4/CD27-. Since it is anticipated that the proportion of CD3+ cells in the final product will approximate 90-95%, there will not be specific subset analysis of CD3– cell populations.

After harvest the tumor-specific T-cells may be purified by any conventional means, such as, e.g., by using density gradient, such as, e.g., a Ficoll medium. A portion of the tumor-specific T-cells may be stored by freezing in a suitable freezing medium after harvesting and purifying the tumor-specific T-cells.

The tumor-specific T-cells obtained by the expansion method described herein may be used in a method for treating the subject suffering from cancer or for effecting tumor regression in a subject having a tumor. The method can include administering to the subject in need thereof an effective amount of tumor-specific T-cells obtained by the expansion method.

The method described herein may be used for treatment of any solid neoplasm, tumor, or cancer of epithelial, mesenchymal or embryological origin in any anatomical location. In some embodiments, the cancer being treated may include sarcomas, carcinomas (e.g., small cell lung cancer, and ovarian cancer), lymphomas, or germ cell tumors. The cancer may include, but is not limited to, ovarian, lung, head, colorectal, rectal, gastric, heart, liver, pancreatic, bladder, prostate, colon, breast, testicular, brain, skin, esophageal, tracheal, head and neck, lymphoid, leukemia, glioblastoma, vulvar, melanoma, mesothelioma, renal, thyroid, soft tissue, and bone cancer. In certain embodiments, the cancer cell may be a melanoma, breast, pancreatic, colorectal, or lung cancer.

The amount of tumor-specific T-cells administered to the subject to treat the tumor or cancer depends on the severity of the disease. In some embodiments, at least 10 million, at least 20 million, at least 30 million, at least 40 million, at least 50 million, at least 60 million, at least 70 million or at least 80 million tumor-specific T-cells can be administered.

The tumor-specific T-cells may be formulated as a pharmaceutical composition suitable for parenteral administration to the patient, such as intravenous, intraarterial, intrathecal, or intraperitonal administration.

When the tumor-specific T-cells are administered parenterally, they may be formulated in an isotonic medium, i.e., in a medium having the same tonicity as blood, and comprising one or more substances preventing aggregation of the cells. A specific example of a medium is a 0.9% NaCl solution comprising up to 3% human serum albumin such as, e.g., up to 2% human serum albumin or up to 1% human serum albumin. For intravenously administration, the concentration of tumor-specific T-cells in the composition to be administered can be within the range from about 0.5 million T-cells/ml medium to about 4 million T-cells/ml medium, such as, e.g., from about 0.5 million T-cells/ml medium to about 3 million T-cells/ml medium, from about 0.5 million T-cells/ml medium to about 2 million T-cells/ml medium or from about 1 million T-cells/ml medium to about 2 million T-cells/ml medium.

The composition comprising the tumor-specific T-cells may be administered as a single dose or multiple doses. It may be infused over 1 to 2 hours.

The treatment method may be performed once or repeated depending on the severity of the disease. Furthermore, the treatment may be reiterated upon recurrence of the disease.

The treatment described herein may be supplemented with any other relevant treatment for cancer. Such supplemental treatment may be given before, at the same time or after the administration of the T-cells and it may be given at frequencies normally used for such treatments. A suitable example of supplemental treatment is chemotherapy and the like.

Other embodiments, described herein relate to kits for use in a method according to the invention, the kit comprising a medium for cultivation of T-cells. The medium may be any suitable serum-free medium, such as, e.g., AIMV, RPMI 1640, DMEM or MEM.

The kit may further comprise one or more substances for stimulating, activating and directing tumor-specific T-cells. Examples of such substances may be VEGF inhibitors, substances capable of activating T-cells, and substances having agonistic activity towards the IL-2 receptor, and/or substances promoting the development of Th1 type T-lymphocytes.

The kit may also comprise a pharmaceutical composition suitable for intravenous administration. The pharmaceutical composition may be mixed with the population of tumor-specific T-cells before administration.

The kit may also comprise one or more syringes comprising a lymph node locator, such as e.g., the ones mentioned above.

The kits may also comprise instructions for use, such as, e.g., instructions in the form of computer software.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In this Example, we determined whether tumor-specific T cells could be cultured and expanded from melanoma-draining regional lymph nodes in patients in stage III who are undergoing completion lymph node dissection after a positive sentinel node biopsy.

Methods

Melanoma-Draining Lymph Node Samples

Adult patients underwent completion lymphadenectomy as part of their standard care for stage III melanoma as determined by a positive sentinel lymphnode biopsy. A tangential portion of 3 lymph nodes were removed from the lymphadenectomy specimen and mechanically separated, creating a single-cell suspension. Cell counts and viability were measured using the improved Neubauer hemocytometer (LWScientific, Lawrenceville, Ga.) and trypan blue staining.

Melanoma-draining lymph node (MDLN) cells that were scheduled to be cryopreserved were first cultured overnight at a concentration of 1 3×10$^6$ cells/mL in complete media (CM) (AIM-V Media, Gibco, Grand Island, N.Y.) with 5% pooled human AB serum (Innovative Research, Novi, Mich.) and 30 U/mL interleukin-2 (IL-2, Invitrogen; Life Technologies, Grand Island, N.Y.) at 378 C with 5% $CO_2$. The following day, cells were centrifuged and resuspended in AIM-V Media with 25% human pooled AB serum and 10% DMSO at a concentration of 10-20 3×10$^6$ cells/mL. Cells were then frozen using a controlled-rate freezer and stored in liquid nitrogen until further analysis.

MDLN Cell Culture Activation In Vitro

Freshly harvested or thawed-cryopreserved MDLN cells were activated with anti-CD3/anti-CD28 beads (Dynal AS, Oslo, Norway) in the presence of 100 U/mL IL-2 or IL-2 with 10 ng/mL interleukin-7 (IL-7, Invitrogen) at a cell density of 2×10$^6$ cells per well in a 24-well plate. Cells were split to a concentration of 0.25×10$^6$ cells/mL by adding fresh CM containing cytokines on days 4, 7, 11, and 14.

Tumor- and Antigen-Presenting Cell Lines

Human melanoma cell lines A375, Sk-mel-28 (Sk-mel), breast cancer cell line MDA-231, and glioma cell line U87 were donated by Dr Bingcheng Wang (Case Western Reserve University, Cleveland, Ohio). Cells were cultured in DMEM with 5% FBS (Gibco). The T2 antigen-presenting cell line was donated by Dr Pierre Triozzi (Cleveland Clinic Foundation, Cleveland, Ohio). Cells were cultured in RPMI with 10% FBS (Gibco).

Flow Cytometry Analyses

MDLN samples were stained with CD3-PE, CD4-FITC, CD8-FITC, CD56, and CD19-FITC (Invitrogen) and fixed with 1% paraformaldehyde prior to being analyzed on LSR II flow cytometer (BD Biosciences, San Jose, Calif.) and the data were processed using WinList (Verity Software House, Topsham, Me.).

Interferon-γ ELISA

Day 14 MDLN cultures were plated in a 96-well plate with A375 cells or melanoma peptide-labeled T2 cells at an effector: stimulator ratio of 2:1 and no IL-2. Cells were cocultured for 72 hours prior to assay of supernatant for Interferon-γ (IFN-γ) levels using ELISA (Thermo Scientific, Rockford, Ill.).

Apoptosis Assays

Day 14 MDLN cultures were incubated with human tumor cells lines in 24-well plate with 2 mL of CM per well and no IL-2. MDLN/tumor cell mixture was stained with CD3-PE in 100 mL staining buffer (BD Pharmingen, San Diego, Calif.) and then with the Annexin V-FITC Apoptosis Stain Kit and 7-AAD (BD Pharmingen) according to the manufacturer's instructions. Cells were analyzed using WinList software (Verity Software House, Topsham, Me.) and gating on the CD3-population to determine early and late apoptosis of the tumor cells.

MDLN Cell Fractionation

Day 14MDLN cultures were labeled with anti-CD8 Microbeads (Miltenyi Biotec, Bergisch Gladbach, Germany) and then separated using LD Magnetic Separation Column (Miltenyi Biotec) into CD8-enriched and CD8-depleted cell populations. The isolation procedure resulted in more than 90% purity in each cell population.

Confocal Fluorescent Microscopy

Day 14 MDLN cells and A375 cells were seeded on a cover slide in a 6-well culture plate at a T cell:tumor cell ratio of 4:1 for 24 hours. The cells were then labeled with anti-CD4-pacific blue, anti-CD8-pacific blue, annexin-FITC, anti-CD3-PE, anti-TCR-FITC, and/or anti-CD43-PE. The fluorescence images were acquired on a Zeiss LSM 510 and processed by Zeiss LSM Image software (Zeiss, Dublin, Germany).

Results

Cryopreservation of MDLN Does Not Significantly Alter Phenotype and Function The ability to cryopreserve patient samples effectively can alleviate issues related to timing of cell infusion and allow for multiple cell infusions. Therefore, we tested the impact of cryopreservation on MDLN cell survival, phenotype, and growth potential. Cell counts throughout the cryopreservation process (after creation of a fresh single-cell suspension, after overnight culture prior to cryopreservation, and after cells were cryopreserved and then thawed at a later date) show that on average 65% (95% CI 45.1-84.9) of cells are recovered (FIG. 2A). Cell loss occurred almost exclusively during the thawing of the cells and not during overnight culture. In order to determine whether specific cell subsets were lost during the cryopreservation process, FACS analysis was performed. A small but significant decrease in B cells from 20.5% to 16.7% (P=0.03) was observed after thawing cryopreserved cells, but there was no significant change in the percentage of CD3, CD4, or CD8. T cells (FIG. 2B). Finally, to determine whether the growth potential of MDLN cells was affected by cryopreservation, cell samples were cultured with IL-2 either fresh or after cryopreservation, and no obvious differences in growth rates were observed (FIG. 2C).

IL-2 and IL-2 with IL-7 Produce Similar MDLN Cultures

Although most regimens of T-cell expansion in vitro involve the use of IL-2, we also were interested in investigating the potential benefit of adding IL-7, which has been shown to support the growth of tumor-specific cytotoxic T cells during long-term culture. IL-2 alone and IL-2/IL-7 resulted in nearly identical growth rates of MDLN cultures (FIG. 3, A), with most cultures achieving greater than 100-fold increase in 14 days. Both IL-2 and IL-2/IL-7 cultures started from the same MDLN and had 60% (95% CI 48.2-71.8) CD3+ T cells. At the end of the 14-day culture period, the percent of CD3+ cells in IL-2 cultures increased to 96% whereas for IL-2/IL-7, the increase in CD3+ cells was to 93% (P=0.03, FIG. 3, B). Day 0 MDLN samples had a CD4/CD8 ratio of 6 (95% CI 4-8), which decreased to 3 (95% CI 1.9-4.1) for IL-2 and 2 (95% CI 1.3-2.7) for IL-2/IL7 by the end of the culture period (P=0.43 for IL-2 versus IL-2/IL-7) (FIG. 2, C). Staining was also performed for CD56 on day 14 in a few patients and was consistently below 5% (data not shown).

The functional capacity of the day 14 MDLN cell cultures was evaluated first by cytokine production and then by in vitro assays of tumor cell apoptosis. Coculture of day 14 MDLN cells with T2 antigen-presenting cells pulsed with human melanoma peptides MART-1 and TRP-2 as well as whole live human melanoma A375 cells resulted in an IFN-γ stimulation index of 8.3, 9.5, and 11.8, respectively, for IL-2 cultures (FIG. 3, D). For MDLN cells grown in IL-2 and IL-7, the stimulation index was 4.6, 5.0, and 3.5, respectively. These results suggest that both culture types contain peptide-reactive T cells with the potential for significant "helper" functions.

In order to determine whether culture-activated T cells had the ability to mediate tumor cell apoptosis in vitro, we performed kinetics and dose response experiments analyzing day 14 MDLN cells cocultured with A375 and Sk-mel melanoma cell lines (FIGS. 4A and B). For A375, MDLN cells increased apoptosis of tumor cells over baseline (tumor cells alone) by 11.7%, 7.5%, and 42.4% for 24, 48, and 72 hours, respectively. For Sk-mel, the increase over baseline was 2.1%, 11%, and 34.9%, respectively. We also observed a dose-response of increase in tumor cell apoptosis with increasing MDLN cell-to-tumor cell ratio (FIG. 4C). Using MDLN cells with the A375 cell line at ratios of 2:1, 4:1, and 10:1, the increase of apoptosis over baseline was 28.9%, 43.1%, and 48.7%, respectively. These results were used to perform all subsequent apoptosis experiments with a T cell:tumor cell ratio of 2:1 assayed at 72 hours.

Day 14 MDLN cells from 4 different patients cultured in IL-2 and IL-2/IL-7 resulted in similar levels of tumor-cell apoptosis for human melanoma lines A375 and Sk-mel (FIG. 5). Day 14 MDLN cells cultured in IL-2 alone increase apoptosis over baseline by 42.3% and 50.6%, respectively ($P<0.001$ for both), whereas those cultured in IL-2 and IL-7 increased apoptosis by 43.2% and 46.6%, respectively ($P<0.03$ for both). When incubated with human brain tumor line U87, IL-2 cultures increased apoptosis by 17.5% ($P=0.71$) and IL-2 and IL-7 increased apoptosis by 33.1% ($P=0.06$). These results suggest that both culture types result in T cells that mediate melanoma specific apoptosis in vitro.

In order to determine whether day-14 MDLN cells from a large number of patients demonstrated melanoma-specific antitumor activity in vitro, apoptosis assays were performed with 2 human melanoma cell lines (A375 and Sk-mel), 1 human breast cancer cell line (MDA-231), and 1 human brain cancer cell line (U87) (FIG. 6). Day-14 MDLN cells mediated a significant increase in apoptosis over baseline, on an average of 27.1% and 29.1% for A375 and Sk-mel, respectively ($P<0.001$). By contrast, MDLN cells resulted in nonsignificant increases over baseline of 14.6% and 14.8% for MDA-231 ($P=0.25$), and U87 ($P=0.18$), respectively, confirming that the cultures contain melanoma specific T cells.

To determine whether MDLN cells physically interacted with tumor cells, we employed confocal fluorescent microscopy. FIG. 7, A, shows annexin V-positive apoptotic A375 tumor cells interacting with T cells labeled with anti-CD3. To further characterize this interaction, MDLN cultures were labeled with either anti-CD4 or anti-CD8 antibodies and with T-cell receptor (TCR) antibodies and CD43 antibodies (FIGS. 7B and C). These images show CD4+ or CD8+ T-cells interacting with unlabeled A375 tumor cells. At the center of the interaction is the TCR, which has been concentrated at the point of interaction, indicating that this is an immunologic synapse. Also noted is that CD43 (a ligand for E-selectin that can also downregulate cell interactions) is excluded from the T cell versus tumor cell interaction.

Because both CD4+ and CD8+ T cells can create an immunologic synapse with A375, the contribution to tumor cell apoptosis from each T-cell population was evaluated. CD8+ T cells were depleted from the standard MDLN culture on day 14, and the tumor cell apoptosis assays were performed (FIG. 8). Unfractionated MDLN cells were capable of increasing A375, Sk-mel, and U87 apoptosis by 44.1%, 56.9%, and 23% over baseline, respectively ($P=0.012$, 0.003, 0.017). The CD8+ fraction of MDLN was able to increase apoptosis of the tumor lines by 18.3%, 31.8%, and 20.5%, respectively ($P=0.018$, 0.06, and 0.015). Interestingly, the CD8-depleted fraction consisting primarily of CD4+ cells was able to increase apoptosis of tumor lines by 23%, 39.1%, and 15.9%, respectively ($P=0.001$, 0.021, and 0.006).

MDLN Cultures Do Not Result in Cell Exhaustion Phenotype

It has been reported that T cells exhibiting surface coexpression of PD-1 and Tim-3 may represent an "exhausted" phenotype with decreased ability to proliferate and perform effector function in response to antigen. FIG. 9 shows that on day 0 of the culture there are minimal exhausted T cells, 0.2% for both CD4+ and CD8+ subsets. Over 14 days in culture, the percentage of CD8+ and CD4+ exhausted T cells increases to 1.2% ($P=ns$) and 2.6% ($P=0.003$), respectively. However, these levels are well below the clinically significant levels seen in tumor-bearing mice, which can approach 50% of T cells.

Example 2

In this Example, we examined the effects of endogenous VEGF on the phenotype and antitumor therapeutic efficacy of effector T cells derived from tumor-draining lymph nodes. Our results confirm that VEGFR1 is expressed on a variety of hematopoietic cells including CD11b and CD11c expressing APC as well as a subpopulation of CD4 T cells, all of which can be influenced by soluble VEGF. Neutralization of VEGF with specific mAb results in the generation of CD4 T helper 1 cells with enhanced tumor-specific interferon-γ secretion in vitro. Prior studies have demonstrated that adoptive transfer of activated tumor draining lymph node cells in the absence of exogenous IL-2 results regression of established tumors, and that the therapeutic effects require participation of CD4. The results of this study demonstrate that VEGF may either directly or indirectly exert inhibitory effects on Th1 cell development and support the concept that reducing concentrations of soluble VEGF may enhance antitumor immune responses.

Materials And Methods

Mice

Female BALB/c mice were purchased from Charles River Laboratories (Wilmington, Mass.) and maintained in a pathogen-free environment for use at the age of 8 to 10 weeks.

Tumor Lines

4T1 is a 6-thioguanine resistant tumor cell line derived from a spontaneous murine mammary carcinoma in BALB/c mice (generously provided by Suzanne Ostrand-Rosenberg, University of Maryland Baltimore County, Baltimore, Md.). It was passaged in tissue culture flasks (Corning Inc., Corning, N.Y.) in complete media (CM) with 10% fetal bovine serum, and was harvested prior to inoculation with trypsin/EDTA.

Activation and Expansion of 4T1 TDLN Cells

BALB/c mice were inoculated subdermally with $1\times10^6$ 4T1 tumor cells in 50 μl of HBSS into both flanks using a 27-gauge needle and syringe. TDLN cells were harvested under sterile conditions on post-inoculation day 9 and dispersed mechanically for culture as a single cell suspension. TDLN cells were then activated in 24 well plates using immobilized anti-CD3 mAb in 2 ml of CM at a concentration of $4 \times 10^6$ cells/well for two days. For cells in the treatment group, 0.5 to 10 μg/ml of rabbit-anti-mouse VEGF mAb (R&D Systems, Minneapolis, Minn.) was added to each well on day 0 of culture. Rabbit IgG at a concentration of 10 μg/ml was used as a control. The activated cells were then harvested, washed, and re-suspended at $1 \times 10^5$ cells/ml in CM with IL-2 (4 IU/ml) on day 2 of culture and expanded for three additional days prior to use for IFN-γ ELISA or adoptive immunotherapy on day 5.

Quantification of Soluble VEGF and Neutralization with Anti-VEGF mAb

The concentration of soluble VEGF in supernatants collected from 4T1 TDLN cells on day 2 and day 5 of culture was determined using a commercially available ELISA kit (Santa Cruz Biotechnology, Santa Cruz, Calif.). Dose-titration experiments were then performed on TDLN cells in culture with anti-VEGF mAb concentrations ranging from 0 to 10 μg/ml in order to determine the optimal concentration of antibody necessary for VEGF neutralization during the activation and expansion of TDLN cells in vitro.

Phenotypic Analysis of TDLN Cells Using Flow Cytometry

The following FITC- and phycoerythrin-conjugated antibodies were used to analyze 4T1 TDLN cells on days 0, 2 and 5 of culture: anti-Thy 1.2, CD4, CD8, CD 25, and CD62L (Pharmingen, San Diego, Calif.). FACS analysis was also performed on freshly harvested (day 0) 4T1 TDLN cells using mAbs against the cell surface determinants for CD11c, CD11b, CD4, CD 8, CD62L as well as VEGFR-1 and VEGFR-2 (Santa Cruz Biotechnology, Santa Cruz, Calif.) to determine VEGF receptor expression on APC and T cell subpopulations. Samples were analyzed using direct immunofluorescence staining of 0.5 to $1 \times 10^6$ cells with both FITC-conjugated mAb and phycoerythrin-conjugated mAb. In each sample, approximately 10,000 cells were evaluated using a FACScan flow microfluorometer (Becton Dickinson, Sunnyvale, Calif.).

Isolation of L-selectin$^{low}$ Cells from TDLNs

Previous studies have demonstrated that the subpopulation of lymphocytes within TDLNs that express low levels of the adhesion molecule CD62L or L-selectin (L-sel) appear to mediate therapeutic antitumor activity in vivo (21, 22). L-sel$^{low}$ cells were separated from freshly harvested TDLNs by negative selection using L-sel immunomagnetic beads and Midi-MACS columns. Cells were incubated with anti-L-sel magnetic beads for 1 hour at room temperature, washed in HBSS, and placed through a Midi-MACS column at a concentration of $100 \times 10^6$ cells/ml. The column was subjected to a magnetic field, and the L-sel$^{low}$ cells were passed through the column with an efficiency of 40-50% and final yield of approximately 10-15%. Following removal of the magnetic field, several exchanges of buffer were added to elute the L-sel$^{high}$ expressing cells. The efficiency of separation was then confirmed by FACS analysis of both L-sel$^{low}$ and L-sel$^{high}$ populations. These cells were then activated and expanded in culture as described above for subsequent use for IFN-γ ELISA or adoptive immunotherapy.

Quantification of Tumor Specific IFN-γ Secretion Using ELISA

Following 5-day culture activation with IL-2 and anti-CD3, unfractionated (UF) or L-sel$^{low}$ TDLN cells were harvested from the control (no anti-VEGF mAb) and treatment (10 μg/ml anti-VEGF mAb) groups and incubated with various stimulators. $2 \times 10^6$ activated 4T1 TDLN cells were incubated with either immobilized anti-CD3 (maximal release) or $1 \times 10^6$ irradiated (3000 cGy, Cesium source) 4T1 cells. 4T1 tumor cells alone were used to determine constitutive secretion of IFN-γ. Twenty-four well plates with a total volume of 2 ml of CM per well were used and cells were incubated at 37° C. for 24 hours. Supernatants from each group were then collected and the concentration of IFN-γ was measured using a commercially available ELISA kit (PharMingen, San Diego, Calif.).

Adoptive Immunotherapy of 3 Day Established 4T1 Pulmonary Tumors

Pulmonary tumors were established by inoculation of BALB/c mice with $1 \times 10^5$ cultured 4T1 tumor cells in 1.0 cc HBSS using tail vein injections and adoptive transfer was performed three days later. Activated TDLN cells were harvested on the day of adoptive transfer (day 5 of culture) and washed and resuspended with HBSS prior to a viability count using trypan blue and hemacytometer. Cells were then diluted to the proper concentration and administered to the tumor-bearing mice in 1 cc of HBSS via tail vein injection. The mice were monitored closely for signs of respiratory distress throughout the experiment and sacrificed between day 17 and 20 post-inoculation. Lungs were harvested at the time of sacrifice and visible pulmonary tumors were enumerated following trans-tracheal perfusion with 15% India ink and fixation with Fekate's solution.

Results

Quantification of Soluble VEGF Levels in 4T1 TDLN Cell Culture and Determination of Optimal Anti-VEGF mAb Concentrations for Neutralization of VEGF In Vitro The levels of soluble VEGF in supernatants collected from 4T1 TDLN cells on day 2 and day 5 of culture were analyzed using ELISA in order to determine both the presence of VEGF in culture and the concentrations of anti-VEGF mAb necessary for its neutralization. In the initial dose-titration experiment, cells were cultured in the presence of anti-VEGF mAb in concentrations ranging from 0 to 5.0 μg/ml. Analysis of supernatant from cells in the control group (no anti-VEGF mAb) demonstrated the presence of soluble VEGF at a concentration of 364 pg/ml on day 2 and 27 pg/ml on day 5 of culture. In contrast, supernatants from cells cultured with anti-VEGF mAb demonstrated near-complete neutralization of VEGF on day 2, irrespective of the concentration of antibody used (6 to 12 pg/ml of VEGF at doses of antibody ranging from 0.5 to 5.0 μg/ml). However, the neutralizing effect of anti-VEGF mAb was transient at these concentrations and did not significantly change VEGF levels in supernatants taken from cells on day 5 of culture (FIG. 10A).

In a subsequent experiment, a higher concentration of anti-VEGF mAb was used (10 µg/ml) and the level of soluble VEGF in supernatants taken from these cells was compared to cells cultured without antibody. As demonstrated in the previous experiment, supernatant from cells in the control group (no anti-VEGF mAb) contained high levels of VEGF on day 2 (305 pg/ml) and minimal levels of VEGF on day 5 (7 pg/ml). However, in contrast to the lower concentrations of antibody used in the previous experiment, 10 µg/ml of anti-VEGF mAb was effective in completely neutralizing all soluble VEGF in supernatants from day 2 and day 5 of culture (FIG. 10B). As a result, all subsequent experiments requiring anti-VEGF mAb were performed using a concentration of 10 µg/ml.

Phenotypic Expression of VEGF Receptor Subtype 1 (VEGFR-1) on 4T1 TDLN Cells

FACS analysis of 4T1 TDLN cells was performed on day 0 in order to determine the phenotypic expression of VEGFR-1/flt-1 on APCs (CD11c, CD11b) and T lymphocytes (CD4, CD8) prior to expansion and activation in vitro. Receptor expression was highest on APCs, with 58% of CD11c and 26% of CD11b cells positive for VEGFR-1. T cells demonstrated much lower levels of receptor expression, with 9.4% of CD4 and 3.4% of CD8 cells positive for VEGFR-1. FACS analysis of VEGF receptor subtype 2 (VEGFR-2/flk-1) on 4T1 TDLN cells showed a lack of phenotypic expression of this receptor on both APC and T cell subpopulations (data not shown).

Proliferation of 4T1 TDLN Cells During Activation and Expansion In Vitro and the Ratio of Activated CD4 and CD8 T Cells Cultured with Anti-VEGF mAb The mean expansion index of 4T1 TDLN cells activated on immobilized anti-CD3 for 48 hours (day 2) followed by incubation with IL-2 (4 IU/ml) for 72 hours (day 5) was determined for cells cultured with and without anti-VEGF mAb. Proliferation of these cells was not changed by the addition of anti-VEGF mAb on day 0 of culture, as demonstrated by a mean expansion index of 3.2× for cells cultured with anti-CD3 antibody alone (control) versus 3.3× for cells cultured with anti-CD3 and anti-VEGF mAb (FIG. 11). However, a phenotypic change in the TDLN cell population on day 5 of culture was observed. FACS analysis of activated T lymphocytes on Day 5 of culture demonstrated an increase in the CD4:CD8 ratio for cells cultured in the presence of anti-VEGF mAb (0.98) compared to cells cultured in the absence of anti-VEGF mAb (0.67) (FIG. 12).

Effect of Neutralizing Anti-VEGF mAb on Tumor-Stimulated IFN-γ Cytokine Secretion by 4T1 TDLN Cells Prior studies of adoptive immunotherapy in both humans and murine models have demonstrated that tumor-stimulated secretion of IFN-γ and generation of T helper 1 cells correlates with anti-tumor efficacy in vivo following adoptive transfer into mice bearing established tumors (13-15). In order to determine whether neutralization of VEGF during T cell culture resulted in functional alterations in cytokine secretion, tumor-stimulated IFN-γ was measured by ELISA. Unfractionated (UF) and L-selectin low (Lsel$^{low}$) TDLN cells cultured in the presence of anti-VEGF mAb demonstrated increased 4T1-stimulated IFN-γ secretion as compared to control TDLN cells cultured in the absence of anti-VEGF mAb. Tumor-stimulated IFN-γ secretion in the UF group was 1355 pg/ml and 473 pg/ml for cells cultured with and without anti-VEGF mAb, respectively. Tumor-specific IFN-γ secretion in the Lsel$^{low}$ group was 3157 pg/ml and 1568 pg/ml for cells cultured with and without anti-VEGF mAb, respectively (FIG. 13). These results confirm that neutralization of VEGF during T cell activation promotes generation of T cells with enhanced cytokine secretion in response to irradiated tumor cell targets.

Antitumor Therapeutic Efficacy of Activated 4T1 TDLN Cells Cultured with Anti-VEGF mAb Against 3 Day Established Pulmonary Tumors In Vivo In order to determine whether TDLN cells activated in the presence of anti-VEGF mAb resulted in T cells with improved effector activity in vivo, activated TDLN cells were adoptively transferred into mice bearing 3-day established pulmonary tumors. As shown in Table 1, adoptive transfer of UF TDLN cells activated in the presence of anti-VEGF mAb resulted in a statistically significant reduction in the mean number of pulmonary tumors compared to similar cells cultured without antibody, with an IgG antibody control or mice receiving HBSS (p<0.01). Mice treated with $5\times10^6$ TDLN cells activated in the presence of anti-VEGF mAb had a mean of 26 tumors versus 190 for the no antibody group and 191 for the IgG antibody control group. Similarly, mice treated with $20\times10^6$ TDLN cells activated in the presence of anti-VEGF mAb had a mean of 17 tumors versus 59 for the no antibody group and 33 for the IgG antibody control group (p<0.01).

TABLE 1

Unfractionated 4T1 TDLN cells cultured in the presence of anti-VEGF mAb demonstrate an enhanced therapeutic effect against 3-day established pulmonary tumors

| TDLN Treatment Group$^a$ | No. Mice per Group | No. Cells Transferred$^b$ | Mean No. Pulmonary Tumors (SEM) |
|---|---|---|---|
| A HBSS Control | 5 | 0 | 228 (49) |
| B No Antibody | 5 | 5 × 10$^6$ | 190 (45) |
| C No Antibody | 5 | 20 × 10$^6$ | 59 (14) |
| D IgG Antibody | 5 | 5 × 10$^6$ | 191 (34) |
| E IgG Antibody | 5 | 20 × 10$^6$ | 33 (9) |
| F anti-VEGF mAb | 5 | 5 × 10$^6$ | 26 (7)$^c$ |
| G anti-VEGF mAb | 5 | 20 × 10$^6$ | 17 (14)$^d$ |

$^a$All cells were harvested from Day 9 TDLN and cultured on immobilized anti-CD3 antibody either with or without rabbit IgG or anti-VEGF mAb 10 µg/ml for 48 hours followed by expansion in IL-2 for an additional 72 hours.
$^b$Adoptive transfer of cells following in-vitro activation and expansion was performed using tail vein injections.
$^c$Statistically significant (p < 0.01) reduction in the mean number of pulmonary tumors at time of sacrifice compared to the same dose of cells cultured with no antibody (group B) or rabbit IgG (group D).
$^d$Statistically significant (p < 0.01) reduction in the mean number of pulmonary tumors at time of sacrifice compared to the same dose of cells cultured with no antibody (group C) or rabbit IgG (group E).

As shown in Table 2, adoptive transfer of Lsel$^{low}$ TDLN cells in the anti-VEGF mAb treatment group also resulted in a reduction in the mean number of pulmonary tumors compared to similar cells cultured without antibody, although this effect was limited to the lower dose of Lsel$^{low}$ TDLN cells. At a dose of 2×10$^6$ cells, mice in the anti-VEGF mAb group had a mean of 25 tumors versus 73 for the no antibody group (p<0.01). By contrast, mice treated with 5×10$^6$ T cells activated in the absence of anti-VEGF mAb were mostly cured, precluding assessment of improved therapeutic efficacy in response to anti-VEGF mAb. These results of experiments using both UF and L-sel$^{low}$ TDLN cells confirm that T cells activated in the presence of anti-VEGF mAb exhibit enhanced therapeutic efficacy against established tumors in vivo.

TABLE 2

L-selectin[low] 4T1 TDLN cells cultured in the presence of anti-VEGF mAb demonstrate enhanced therapeutic effect against 3-day established pulmonary tumors

| TDLN Treatment Group[a] | No. Mice per Group | No. Cells Transferred[b] | Mean No. Pulmonary Tumors (SEM) |
|---|---|---|---|
| A HBSS Control | 5 | 0 | 221 (47) |
| B No Antibody | 5 | $2 \times 10^6$ | 73 (26) |
| C No Antibody | 5 | $5 \times 10^6$ | 2 (2) |
| D anti-VEGF mAb | 5 | $2 \times 10^6$ | 25 (9)[c] |
| E anti-VEGF mAb | 5 | $5 \times 10^6$ | 3 (3) |

[a]L-selectin[low] cells were harvested from Day 9 TDLN, fractionated using a midi-MACS column, and cultured on immobilized anti-CD3 antibody either with or without anti-VEGF mAb 10 µg/ml for 48 hours followed by expansion in IL-2 for an additional 72 hours.
[b]Adoptive transfer of cells following in vitro activation and expansion was performed using i.v. tail vein injections.
[c]Statistically significant ($p < 0.01$) reduction in the mean number of pulmonary tumors at time of sacrifice compared to the same dose of TDLN cells cultured with no antibody (group B).

Example 3

Pancreatic cancer is the 4th leading cause of cancer death with an overall 5-year survival of only 7%. In this example, we expanded tumor-reactive T-cells from pancreatic cancer draining lymph nodes (PDLNs) derived from patients undergoing surgery for pancreatic adenocarcinoma. Our goal was to develop a method of ex vivo expansion of PDLNs as a source of effector T-cells for adoptive immunotherapy.

Methods

PDLN Procurement

Under an IRB-approved protocol (CASE 7212), PDLN tissues were collected at the time of a regularly planned pancreatic cancer surgery. Once the specimen was removed, it was placed on a back table where a portion of two regional lymph nodes were randomly sampled with the goal to avoid nodes with suspected metastatic adenocarcinoma.

Once the samples were collected, they were mechanically separated under sterile conditions and passed through a 70 µm filter, creating a single cell suspension. The number of viable cells was then determined using trypan blue and a hemocytometer. PDLN cells were then placed in AIM-V culture medium (Life Technologies, Grand Island, N.Y.) completed with 10% heat inactivated pooled human AB serum (Innovative Research, Novi, Mich.) by volume, at a concentration of $10^6$ cells/mL with recombinant human IL2 (Prometheus Laboratories, San Diego, Calif.) at 30 IU/mL overnight. The next day, the cells were centrifuged and cryopreserved using freezing media (65% AIM-V, 25% pooled heat inactivated human AB serum, 10% DMSO) for future expansion.

PDLN Cell Ex Vivo Activation and Expansion

PDLN cells to be expanded were thawed and resuspended at a concentration of $10^6$ cells/mL in completed AIM-V growth medium and activated ex vivo with anti-CD3/anti-CD28 coated beads (Miltenyi Biotec, Auburn, Calif.) at 25 µl/$10^6$ cells and recombinant human IL2 at 100 IU/mL for 72 hours. Cells were then expanded for 14 days by counting on days 4, 7, and 11 with addition of fresh completed AIM-V to achieve a concentration of $0.25 \times 10^6$ cells/mL as well as addition of 100 IU/mL of IL2.

Surface Phenotypic Analyses

During our culture period, the surface phenotypes were analyzed on days 0, 7, 11, and 14. After counting the cells on each given day, an aliquot of cells was removed for analysis. These cells were pelleted and then resuspended with stain buffer (BD Biosciences, San Jose, Calif.) at $2 \times 10^5$ cells/100 µl. Cells were then stained for CD3, CD4, CD8, CD19, CD56, CD11b, CD11c, CD25, CD45RA, CD45RO, FoxP3, CD27, CCR7, and CD62L in various combinations using flourochrome conjugated monoclonal antibodies (BD Biosciences, San Jose, Calif.). Appropriate isotype controls were utilized when needed. Stained cells were then fixed with fixation buffer (4% paraformaldehyde in PBS) and analyzed on a BD LSR II flow cytometer (BD Biosciences, San Jose, Calif.) and data was analyzed and processed using WinList (Verity Software House, Topsham, Me.).

Tumor Cell Lines

Human pancreatic cancer cell lines AsPc-1 and MIA PaCa-2, melanoma cell line A375, and malignant glioma cell line U87 were cultured in vitro. AsPc-1 was cultured in RPMI with 5% FBS (Life Technologies, Grand Island, N.Y.). MIA PaCa-2 was cultured in DMEM with 5% FBS and 2.5% heat inactivated horse serum (Life Technologies, Grand Island, N.Y.). A375 and U87 were cultured in DMEM with 5% FBS (Life Technologies, Grand Island, N.Y.). Cell lines were split or harvested when they reached 70-80% confluence using 0.05% trypsin (Life Technologies, Grand Island, N.Y.).

Intracellular Phenotypic Analysis

In order to assess the function of activated PDLN cells and their reaction when exposed to pancreatic cancer antigens, the intracellular cytokine expression of IL2, IFNγ, TNF, IL4, IL9 and IL17 by CD4 and CD8 T-cells in the presence and absence of the pancreatic cancer cell line AsPc-1 was determined. Day 11 cultured PDLN cells were co-cultured for 72 hours with AsPc-1. After co-culture, GolgiStop (BD Biosciences, San Jose, Calif.) was added for an overnight culture. Cells were then stained for the surface markers CD4-Pac Blue and CD8-FITC. This was followed by fixation and permeabilization with CytoFix/CytoPerm (BD Biosciences, San Jose, Calif.). After permeabilization, cells were stained intracellularly with either IFNγ-PE, TNF-PE, IL2-PE, IL4-APC, IL9-APC, or IL17A-AF647 (BD Biosciences, San Jose, Calif.). Intracellularly stained cells were analyzed on a BD LSR II flow cytometer and data was processed and analyzed using WinList software.

Apoptosis Assays

In order to determine the ability of the human PDLN to kill cancer cell lines in vitro, we performed co-culture experiments of Day 14 activated PDLN cells against the pancreatic cancer cell lines AsPc-1 and MIA PaCa-2, and for controls, the malignant melanoma cell line A375 and the malignant glioma cell line U87 in 24 well plates.

Two conditions were used to assess the anti-tumor activity of the PDLN cells. The first was a 72-hour direct co-culture in completed AIM-V with 100 IU/mL of IL2 with a T cell to tumor cell ratio of 2:1. The second had identical conditions except that it utilized a Transwell plate insert (Corning, Corning, N.Y.), which separated the PDLN cells from the tumor cells with a 0.4 µm microporous membrane. Control conditions were tumor cells alone or PDLN cells alone. By blocking cell contact and preventing direct cell-cell mediated apoptosis, while still allowing the passage of soluble antigens and cytokines, cytokine mediated tumor apoptosis was examined.

After 72-hour co-culture, the PDLN/tumor cell mixtures were stained with CD3-Pacific Blue in 100 µL of stain buffer (BD Biosciences, San Diego, Calif.) followed by staining with the PE-Annexin V Apoptosis Detection Kit I (BD Biosciences, San Diego, Calif.) and 7-AAD per manufacturer instructions. Cells were then analyzed on a BD LSR II flow cytometer and data was processed and analyzed on Winlist software with exclusion of CD3+ T cells to determine tumor cell apoptosis.

In Vivo PDLN Trafficking

In order to determine the in vivo trafficking of the activated PDLN cells, a heterotopic human pancreatic cancer bearing murine xenograft was established by injecting $1 \times 10^6$ cells of the human pancreatic cancer cell line AsPc-1 in the flanks of NOD/SCID mice. A single dose of $40 \times 10^6$ Day 14 activated PDLN cells was administered via tail vein injection 40 days after tumor inoculation, when the tumors were approximately 10 mm×10 mm. After treatment, tumor size and overall health were monitored per institutional animal resource center guidelines. Mice were euthanized when the primary tumor reached a size greater than 2 cm in any dimension or if they showed signs of illness. After euthanasia, the bone marrow, spleen, and tumor were removed and examined for the presence of human T-cells by both mechanical dispersion followed by flow cytometry and histology sectioning with immunohistochemical (IHC) staining for CD4 and CD8.

In Vivo Intraperitoneal Treatment Model

In order to determine the in vivo therapeutic activity of the activated PDLN cells, a human pancreatic cancer bearing murine xenograft was established by injecting $1 \times 10^5$ cells of the human pancreatic cancer cell line AsPc-1 intraperitoneally into nine NOD/SCID mice. Seven days after tumor inoculation, five mice were randomly selected to receive an intraperitoneal injection of $40 \times 10^6$ Day 14 activated PDLN cells and an additional $40 \times 10^6$ Day 14 activated PDLN cells three days later. The mice were then monitored for overall health and euthanized when showing signs illness per institutional animal resource center guidelines. After euthanasia, necropsies were performed to evaluate for tumor burden and associated sequelae.

Results

PDLN Procurement and Growth

Portions of two regional lymph nodes grossly uninvolved by tumor were collected from 26 patients undergoing pancreatectomy for pancreatic cancer. All lymph nodes were collected from either the peri-portal, hepatic artery, or peripancreatic nodes. The average yield was $110 \times 10^6$ cells/node.

The average expansion of 15 of our PDLN cultures from tissues of 13 patients demonstrates consistent logarithmic growth, with an average 162-fold expansion over 14 days (FIG. 14).

Cell Surface Marker Expression

During our culture period, the surface phenotypes were examined on culture days 0, 7, 11, and 14. When day 0 PDLN surface phenotypes were compared to day 14 cells, there was an increase to >90% T cells as indicated by the marker CD3, with an approximate 3:1 ratio of CD4 to CD8 cells by day 14 (FIG. 15). In addition, there was near complete depletion of CD19+ B cells, CD56+ NK cells, and CD11b+ macrophages. With respect to the T cell population, there was a decrease in CD45RA+ and an increase in CD45RO+ cells, indicating a shift from naïve to activated T cells. In addition to the increase and activation of T cells, our culture conditions did not promote generation of regulatory T cells as there was no significant population of CD4/CD25/FoxP3 triple positive cells.

Intracellular Cytokine Expression

In order to assess the functional aspects of our PDLN cells, we analyzed the expression of numerous intracellular cytokines in a 5 patient subset. We first examined the baseline percentage of cells expressing IL2, IFNγ, TNF, IL4, IL9, and IL17. The same PDLN cells were then co-cultured with the pancreatic cancer cell line AsPc-1 to determine the tumor stimulated cytokine profile. Our results showed a shift towards a Th1/Tc1 phenotype when the PDLN cells were exposed to AsPc1, with a statistically significant increased percentage of cells expressing IL2, IFNγ, and TNF over baseline, from 47% to 66.6%, 21.1% to 29%, and 20% to 24.6% respectively (FIG. 16).

Apoptosis

We next examined the PDLN functional activity against tumor cell lines using a 5 patient subset of our PDLNs. Our results showed that when PDLN cells were directly co-cultured with pancreatic and non-pancreatic cancer cell lines, there was increased apoptosis not only of the pancreatic cancer cell lines AsPc-1 and MIA PaCa-2, but also of the malignant melanoma cell line A375 and the malignant glioma cell line U87. However, when Transwell plate inserts were used to separate the tumor cells from the PDLN cells, a pattern of pancreatic cancer specific apoptosis emerged. High levels of apoptosis were again seen in the pancreatic cancer cell lines AsPc-1 (5.9% to 29.4%) and MIA PaCa-2 (15.5% to 21.1%), but apoptosis of U87 and A375 was abrogated to near baseline levels (FIG. 17). These results suggest the presence of pancreatic cancer-reactive T cells within the polyclonal ex vivo activated PDLN as well as the possibility of alloreactive T cells, which might explain the non-specific killing of several unrelated human tumor cell lines.

In Vivo T-cell Trafficking

In order to assess the in vivo trafficking of the PDLN cells, we examined our AsPc-1 NOD/SCID heterotopic xenograft for the presence of human T cells after adoptive transfer. Control and treated mice were euthanized 3 weeks post-T cell infusion with procurement of bone marrow, spleen and tumor at that time to look for human T cells. Bone marrow and spleen did not show any T cells. However, when the tumors from T cell treated mice were compared to control mice by flow cytometry, it was noted that in two separate samples there was a population representing 0.6% of all cell events that appeared in FSC and SSC region of human lymphocytes. When these were further analyzed, it was found to be 60% CD3 positive, with an approximate 3:1 ratio of CD4 to CD8 (FIG. 18). When control tumors were compared to Day 14 activated PDLN treated tumors using IHC staining, scattered infiltrates of CD4+ and CD8+ positive cells were present in the treated tumors but not in the control tumors, with a predominant CD8+ infiltrate (FIG. 19). This result showed that infused activated PDLN cells traffic to and persist in the tumor, suggesting a degree of tumor antigen specificity.

In Vivo Intraperitoneal Treatment Model

In order to assess the in vivo activity of the PDLN cells, we examined their effect on survival as well as tumor burden. Control and treated mice were euthanized when showing signs of illness per animal resource center guidelines. All control mice were euthanized 44 to 49 days post-tumor inoculation with a mean survival of 45.75 days. In contrast, the mice in the treatment group all survived until the end of the experiment at 85 days, when they were euthanized despite being asymptomatic to evaluate them for tumor burden (FIG. 20). In addition to the marked difference in survival, every mouse in the control group was noted to have hemorrhagic ascites during their necropsy, while the treatment group did not have any evidence of ascites (FIG. 21). When the peritoneal cavity was inspected, all control mice were noted to have carcinomatosis. Inspection of the peritoneal cavity of the treatment group revealed isolated peritoneal tumors in three mice and no evidence of intraperitoneal tumor in two mice (FIG. 22). This result showed that intraperitoneal infusion of activated PDLN cells have anti-tumor activity and can improve overall survival.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating cancer in a subject, the method comprising:
    obtaining tumor draining lymph node (TDLN) tissue from the subject wherein the TDLNs drain a tumor and/or a cancer metastasis of the subject;
    obtaining an enriched population of tumor-specific T-cells from the TDLN tissue, wherein tumor-specific T-cells are specific to the tumor and/or cancer metastasis of the subject;
    activating and expanding tumor-specific T-cells by contacting the enriched population of tumor-specific T-cells ex-vivo with: an anti-CD3 antibody, an anti-CD28 antibody,
    and/or functional fragments thereof, a VEGF inhibitor and optionally an IL-2 receptor agonist, at amounts effective to activate and expand the tumor-specific T-cells; and
    administering the activated and expanded tumor-specific T-cells to the subject.

2. The method of claim 1, wherein the enriched population of tumor-specific T-cells is obtained from TDLNs of the subject with a metastatic cancer.

3. The method of claim 1, wherein the metastatic cancer comprises at least one of melanoma, breast cancer, pancreatic cancer, lung cancer, and colorectal cancer.

4. The method of claim 1, further comprising contacting the enriched population of tumor-specific T-cells ex-vivo with at least one IL-2 receptor agonist.

5. The method of claim 4, wherein the at least one substance IL-2 receptor agonist is IL-2.

6. The method of claim 1, wherein the VEGF-inhibitor is selected from neutralizing monoclonal antibodies against VEGF or its receptor, small molecule tyrosine kinase inhibitors of VEGF receptors, soluble VEGF receptors which act as decoy receptors for VEGF and ribozymes which specifically target VEGF mRNA or combinations thereof.

7. The method of claim 6, wherein the antibody is bevacizumab.

8. The method of claim 1, further comprising obtaining the TDLN tissue from the subject by resecting one or more of the TDLNs from the subject.

9. The method of claim 8, wherein the resected TDLNs are cryopreserved after resection and then thawed prior to obtain an enriched population of tumor-specific T-cells.

10. The method of claim 9, wherein the resected lymph nodes are cultured with IL-2 prior to cryopreservation.

11. The method of 1, wherein the activated and expanded tumor-specific T-cell population is washed, and resuspended in a solution that does not include a VEGF-inhibitor for administration into the subject.

12. A method of treating pancreatic cancer in a subject, the method comprising:
    obtaining pancreatic cancer draining lymph node (PDLN) tissue from the subject;
    obtaining an enriched population of tumor-specific T-cells from the PDLN tissue, wherein the tumor-specific T-cells are specific to pancreatic cancer of the subject;
    activating and expanding tumor-specific T-cells by contacting the enriched population of tumor-specific T-cells ex-vivo with: an anti-CD3 antibody, an anti-CD28 antibody, and/or functional fragments thereof, a VEGF inhibitor and optionally an IL-2 receptor agonist, at amounts effective to activate and expand the tumor-specific T-cells; and
    administering the activated and expanded tumor-specific T-cells to the subject.

13. The method of claim 12, wherein the PDLN tissue is obtained from a subject undergoing surgery for pancreatic adenocarcinoma.

14. The method of claim 12, wherein the IL-2 receptor agonist is IL-2.

15. The method of claim 12, wherein the VEGF-inhibitor is selected from neutralizing monoclonal antibodies against VEGF or its receptor, small molecule tyrosine kinase inhibitors of VEGF receptors, soluble VEGF receptors which act as decoy receptors for VEGF and ribozymes which specifically target VEGF mRNA or combinations thereof.

16. The method of claim 15, wherein the neutralizing monoclonal antibodies against VEGF is bevacizumab.

17. The method of claim 12, further comprising obtaining the PDLN tissue from the subject by resecting one or more of the lymph nodes draining pancreatic cancer in the subject.

18. The method of claim 17, wherein the resected lymph nodes are cryopreserved after resection and then thawed prior to obtaining an enriched population of tumor-specific T-cells.

19. The method of claim 18, wherein the resected lymph nodes are cultured with IL-2 prior to cryopreservation.

20. The method of 12, wherein the activated and expanded tumor-specific T-cell population is washed, and resuspended in a solution that does not include a VEGF-inhibitor for administration into the subject.

21. The method of 1, wherein the activated and expanded tumor-specific T-cell population is washed, and resuspended in a solution that does not include a VEGF-inhibitor for administration into the subject.

\* \* \* \* \*